United States Patent [19]
Celeste et al.

[11] Patent Number: 5,635,372
[45] Date of Patent: Jun. 3, 1997

[54] BMP-15 COMPOSITIONS

[75] Inventors: Anthony J. Celeste, Hudson; Jennifer L. Dube, Arlington, both of Mass.; Karen M. Lyons, Sherman Oaks, Calif.; Brigid Hogan, Brentwood, Tenn.

[73] Assignees: Genetics Institute, Inc., Cambridge, Mass.; Vanderbilt University, Nashville, Tenn.

[21] Appl. No.: 446,924

[22] Filed: May 18, 1995

[51] Int. Cl.$^6$ .............. C12P 21/06; C12N 5/00; C12N 15/00; C07H 21/04
[52] U.S. Cl. ............... 435/69.1; 435/252.3; 435/320.1; 435/325; 435/358; 435/360; 536/23.4; 536/23.5
[58] Field of Search ............... 435/69.1, 240.1, 435/252.3, 320.1; 536/23.4, 23.5

[56] References Cited

U.S. PATENT DOCUMENTS

| | | | |
|---|---|---|---|
| 4,419,446 | 12/1983 | Howley et al. | 435/68 |
| 5,013,649 | 5/1991 | Wang et al. | 435/69.1 |
| 5,106,748 | 4/1992 | Wozney et al. | 435/252.3 |
| 5,108,922 | 4/1992 | Wang et al. | 435/240.2 |
| 5,116,738 | 5/1992 | Wang et al. | 435/69.1 |
| 5,141,905 | 8/1992 | Rosen et al. | 435/69.1 |
| 5,187,076 | 2/1993 | Wozney et al. | 435/69.1 |
| 5,324,819 | 6/1994 | Oppermann et al. | 530/350 |
| 5,366,875 | 11/1994 | Wozney et al. | 435/69.1 |
| 5,393,739 | 2/1995 | Bentz et al. | 514/12 |
| 5,459,047 | 10/1995 | Wozney et al. | 435/69.1 |
| 5,516,654 | 5/1996 | Israel | 435/69.1 |

FOREIGN PATENT DOCUMENTS

| | | |
|---|---|---|
| WO91/18098 | 11/1991 | WIPO . |
| WO93/00432 | 1/1993 | WIPO . |
| WO93/16099 | 8/1993 | WIPO . |
| WO94/01557 | 1/1994 | WIPO . |
| WO94/15949 | 7/1994 | WIPO . |
| WO94/15965 | 7/1994 | WIPO . |
| WO94/21681 | 9/1994 | WIPO . |
| WO94/26892 | 11/1994 | WIPO . |
| WO94/26893 | 11/1994 | WIPO . |
| WO95/01802 | 1/1995 | WIPO . |
| WO95/01801 | 1/1995 | WIPO . |

OTHER PUBLICATIONS

Gething and Sambrook, Nature 293:620–625 (1981).
Kaufman et al., Mol. Cell Biol. 5(7):1750–1759 (1985).
Miller et al., Genetic Engineering 8:277–298 (Plenum Press 1986).
Gentry et al., Mol Cell Biol. 8:4162 (1988).
Derynck et al., Nature 316:701 (1985).
Thies et al., J. Bone & Min. Res., 5:305 (1990).
Thies et al., Endocrinology 130:1318 (1992).
Sampath and Reddi, PNAS, 80:6591–6595 (1983).
Reddi et al., PNAS 69:1601 (1982).
Ham and Cormack, Histology (JB Lippincott Co. 1979), pp. 367–369.
Okayama et al., Mol. Cell Biol. 2:161–170 (1982).
Gough et al., EMBO J. 4:645–653 (1985).
Wong et al., Science 228:810–815 (1985).
Kaufman, R.J., PNAS 82:689–693 (1985).
Morinaga et al., Biotechnology 84:636 (1984).
Taniguchi et al., PNAS 77:5230–5233 (1980).
Kaufman and Sharp, Mol. Cell. Biol. 2:1304 (1982).
Kaufman and Sharp, J. Mol. Biol. 159:601–619 (1982).
Oakley et al., Anal. Biochem. 105:361 (1980).
Laemmli, Nature 227:680 (1970).
Towbin et al., PNAS 76:4350 (1979).
Wozney, J.M. (1992) Mol. Repro. Dev. 32(2): 160–167.
Cunningham et al. (1995) Growth Factors 12(2): 99–109.
Hogan, B. (1996) Curr. Opin. Genet. Dev. 6(4): 432–438.

*Primary Examiner*—Robert A. Wax
*Assistant Examiner*—Lisa J. Hobbs
*Attorney, Agent, or Firm*—Steven R. Lazar; Thomas J. DesRosier

[57] ABSTRACT

Purified BMP-15-related proteins and processes for producing them are disclosed. DNA molecules encoding the BMP-15-related proteins are also disclosed. The proteins may be used in the treatment of bone and cartilage and/or other connective tissue defects and in wound healing and related tissue repair.

17 Claims, No Drawings

BMP-15 COMPOSITIONS

The present invention relates to a novel family of purified proteins designated BMP-15 and BMP-15-related proteins, DNA encoding them, and processes for obtaining them. These proteins may be used to induce bone and/or cartilage or other connective tissue formation, and in wound healing and tissue repair. These proteins may also be used for augmenting the activity of other bone morphogenetic proteins.

BACKGROUND OF THE INVENTION

The search for the molecule or molecules responsible for the bone-, cartilage-, and other connective tissue-inductive activity present in bone and other tissue extracts has led to the discovery of a novel set of molecules called the Bone Morphogenetic Proteins (BMPs). The structures of several proteins, designated BMP-1 through BMP-14, have previously been elucidated. The unique inductive activities of these proteins, along with their presence in bone, suggests that they are important regulators of bone repair processes, and may be involved in the normal maintenance of bone tissue. There is a need to identify whether additional proteins exist which play a role in these processes. The present invention relates to the identification of such a protein, which the inventors have designated BMP-15.

SUMMARY OF THE INVENTION

As used herein, the term "BMP-15-related protein" refers to the human BMP-15 protein, having the amino acid sequence specified in SEQUENCE ID NO:4, as well as homologues of this protein found in other species; and other proteins which are closely related structurally and/or functionally to BMP-15. Examples of "BMP-15-related proteins"include murine PC-3 protein, having the amino acid sequence of SEQUENCE ID NO:2, as well as homologues in other species, particularly human.

Murine PC-3

The murine PC-3 DNA sequence (SEQ ID NO: 1) and amino acid sequence (SEQ ID NO: 2) are set forth in the Sequence Listings. BMP-15-related proteins are capable of inducing the formation of cartilage, bone, or other connective tissue, or combinations thereof. PC-3 proteins may be further characterized by the ability to demonstrate cartilage and/or bone and/or other connective tissue formation activity in the rat bone formation assay described below.

Murine PC-3 may be produced by culturing a cell transformed with a DNA sequence comprising nucleotide a DNA sequence encoding the mature PC-3 polypeptide, comprising nucleotide #634 to nucleotide #1008 as shown in SEQ ID NO: 1, and recovering and purifying from the culture medium a protein characterized by the amino acid sequence comprising amino acids #1 to #125 as shown in SEQ ID NO:2 substantially free from other proteinaceous materials with which it is co-produced. For production in mammalian cells, the DNA sequence further comprises a DNA sequence encoding a suitable propeptide 5' to and linked in frame to the nucleotide sequence encoding the mature PC-3 polypeptide. The propeptide may be the native PC-3 propeptide, or may be a propeptide from another protein of the TGF-β superfamily.

It is expected that other species, particularly human, have DNA sequences homologous to murine PC-3. The invention, therefore, includes methods for obtaining the DNA sequences encoding human PC-3, the DNA sequences obtained by those methods, and the human protein encoded by those DNA sequences. This method entails utilizing the murine PC-3 nucleotide sequence or portions thereof to design probes to screen libraries for the human gene or coding sequences or fragments thereof using standard techniques. Thus, the present invention includes DNA sequences from other species, particularly, human, which are homologous to murine PC-3 and can be obtained using the murine PC-3 sequence. A DNA sequence encoding the complete mature human BMP-15 protein (SEQ ID NO:3) and the corresponding amino acid sequence (SEQ ID NO:4) are set forth herein. As described herein, these sequences were isolated using a portion of the murine PC-3 sequence as a probe. The human BMP-15 sequence of SEQUENCE ID NO:3 may also be used in order to design probes to obtain the complete human BMP-15 gene or coding sequences through standard techniques. The murine PC-3 and human BMP-15 sequences, or portions thereof, may also be used as probes, or to design probes, in order to obtain other related DNA sequences. The BMP-15-related proteins of the present invention, such as human BMP-15, may be produced by culturing a cell transformed with the correlating DNA sequence, such as the BMP-15 DNA sequence, and recovering and purifying protein, such as BMP-15, from the culture medium. The purified expressed protein is substantially free from other proteinaceous materials with which it is co-produced, as well as from other contaminants. The recovered purified protein is contemplated to exhibit cartilage and/or bone and/or connective tissue formation activity. The proteins of the invention may be further characterized by the ability to demonstrate cartilage and/or bone and/or other connective tissue formation activity in the rat bone formation assay described below.

Another aspect of the invention provides pharmaceutical compositions containing a therapeutically effective amount of a BMP-15-related protein, such as murine or human PC-3 or BMP-15 protein, in a pharmaceutically acceptable vehicle or carrier. These compositions of the invention may be used in the formation of bone. These compositions may further be utilized for the formation of cartilage, or other connective tissue, including tendon, ligament, meniscus and other connective tissue, as well as combinations of the above, for example regeneration of the tendon-to-bone attachment apparatus. The compositions of the present invention, such as compositions of human BMP-15, may also be used for wound healing and tissue repair. Compositions of the invention may further include at least one other therapeutically useful agent such as the BMP proteins BMP-1, BMP-2, BMP-3, BMP-4, BMP-5, BMP-6 and BMP-7, disclosed for instance in U.S. Pat. Nos. 5,108,922; 5,013,649; 5,116,738; 5,106,748; 5,187,076; and 5,141,905; BMP-8, disclosed in PCT publication WO91/18098; and BMP-9, disclosed in PCT publication WO93/00432, BMP-10, disclosed in PCT application WO94/26893; BMP-11, disclosed in PCT application WO94/26892, or BMP-12 or BMP-13, disclosed in co-pending patent application, Ser. No. 08/362,670, filed on Dec. 22, 1994. Other compositions which may also be useful include Vgr-2, and any of the GDFs, including those described in PCT applications WO94/15965 WO94/15949; WO95/01801; WO95/01802; WO94/21681; WO94/15966; and others. Also useful in the present invention may be BIP, disclosed in WO94/01557; and MP52, disclosed in PCT application WO93/16099. The disclosures of all of the above applications are hereby incorporated by reference.

The compositions of the invention may comprise, in addition to a BMP-15-related protein, other therapeutically useful agents including growth factors such as epidermal growth factor (EGF), fibroblast growth factor (FGF), transforming growth factor (TGF-α and TGF-β), activins, inhibins, and insulin-like growth factor (IGF). The compositions may also include an appropriate matrix for instance, for supporting the composition and providing a surface for bone and/or cartilage and/or other connective tissue growth. The matrix may provide slow release of the osteoinductive protein and/or the appropriate environment for presentation thereof.

The BMP-15-related compositions may be employed in methods for treating a number of bone and/or cartilage and/or other connective tissue defects, periodontal disease and healing of various types of tissues and wounds. The tissue and wounds which may be treated include epidermis, nerve, muscle, including cardiac muscle, and other tissues and wounds. These methods, according to the invention, entail administering to a patient needing such bone and/or cartilage and/or other connective tissue formation, wound healing or tissue repair, an effective amount of a BMP-15-related protein. The BMP-15-related compositions may also be used to treat or prevent such conditions as osteoarthritis, osteoporosis, and other abnormalities of bone, cartilage or other connective tissue and other tissues. These methods may also entail the administration of a protein of the invention in conjunction with at least one other BMP protein as described above. In addition, these methods may also include the administration of a BMP-15-related protein with other growth factors including EGF, FGF, TGF-α, TGF-β, activin, inhibin and IGF.

Still a further aspect of the invention are DNA sequences coding for expression of a BMP-15-related protein. Such sequences include the sequence of nucleotides in a 5' to 3' direction illustrated in SEQ ID NO: 3, DNA sequences which, but for the degeneracy of the genetic code, are identical to the DNA sequence SEQ ID NO: 3, and encode the protein of SEQ ID NO: 4. Further included in the present invention are DNA sequences which hybridize under stringent conditions with the DNA sequence of SEQ ID NO: 3 and encode a protein having the ability to induce the formation of cartilage and/or bone and/or other connective tissue. Preferred DNA sequences include those which hybridize under stringent conditions [see, T. Maniatis et al, *Molecular Cloning (A Laboratory Manual)*, Cold Spring Harbor Laboratory (1982), pages 387 to 389]. It is generally preferred that such DNA sequences encode a polypeptide which is at least about 80% homologous, and more preferably at least about 90% homologous, to the mature human BMP-15 amino acid sequence shown in SEQ ID NO:4. Finally, allelic or other variations of the sequences of SEQ ID NO: 3, whether such nucleotide changes result in changes in the peptide sequence or not, but where the peptide sequence still has BMP-15 activity, are also included in the present invention.

A further aspect of the invention includes vectors comprising a DNA sequence as described above in operative association with an expression control sequence therefor. These vectors may be employed in a novel process for producing a BMP-15-related protein of the invention in which a cell line transformed with a DNA sequence encoding a BMP-15-related protein in operative association with an expression control sequence therefor, is cultured in a suitable culture medium and a BMP-15-related protein is recovered and purified therefrom. This process may employ a number of known cells both prokaryotic and eukaryotic as host cells for expression of the polypeptide. The vectors may be used in gene therapy applications. In such use, the vectors may be transfected into the cells of a patient in vitro, and the cells may be reintroduced into a patient. Alternatively, the vectors may be introduced into a patient in vivo through targeted transfection.

The purified proteins of the present inventions may be used to generate antibodies, either monoclonal or polyclonal, to human BMP-15 and/or other BMP-15-related proteins, using methods that are known in the art of antibody production. Thus, the present invention also includes antibodies to human BMP-15 and/or other BMP-15 related proteins. The antibodies may be useful for purification of BMP-15 and/or other BMP-15 related proteins, or for inhibiting or preventing the effects of BMP-15 related proteins. The proteins or compositions of the present invention may also be useful for treating cell populations, such as embryonic cells or stem cell populations, to enhance or enrich the growth and/or differentiation of the cells. The treated cell populations may be useful for gene therapy applications.

Description of the Sequences

SEQ ID NO:1 is a nucleotide sequence encoding the entire mature murine PC-3.

SEQ ID NO:2 is the amino acid sequence containing the mature murine PC-3 polypeptide.

SEQ ID NO:3 is a nucleotide sequence encoding the entire mature human BMP-15.

SEQ ID NO:4 is the amino acid sequence containing the mature human BMP-15 polypeptide.

SEQ ID NO:5 is a consensus sequences of members of the BMP/TGF-β/Vg-1 family of proteins; wherein the first Xaa is either Gln, Asn or Asp; the second Xaa is either Asp, Glu or Asn; and the third Xaa is either Val or Ile.

SEQ ID NO:6 is primer #1, directed to the consensus sequence of SEQ ID NO:5.

SEQ ID NO:7 is a consensus sequence of members of the BMP/TGF-μ/Vg-1 family of proteins; wherein the Xaa is either Val or Leu SEQ ID NO:8 is primer #2, directed to the consensus sequences of SEQ ID NO:7.

SEQ ID NO: 9 is the nucleotide sequence of a fragment of murine PC-3 isolated using the primers of SEQ ID NO: 6 and SEQ ID NO:8.

SEQ ID NO:10 is the derived amino acid sequence encoded by the nucleotide sequence of SEQ ID NO:9.

SEQ ID NO:11 is the nucleotide sequence of oligonucleotide primer #3, directed to the murine PC-3 DNA sequence, used to isolate a full-length mPC-3 gene.

SEQ ID NO:12 is the nucleotide sequence of oligonucleotide primer #4, directed to the murine PC-3 DNA sequence, used to isolate a full-length mPC-3 gene.

SEQ ID NO: 13 is the nucleotide sequence of oligonucleotide primer #5, directed to the murine PC-3 DNA sequence, used to isolate a full-length human BMP-15 gene.

SEQ ID NO:14 is the nucleotide sequence of oligonucleotide primer #6, directed to the murine PC-3 DNA sequence, used to isolate a full length human BMP-15 gene.

Detailed Description of the Invention

BMP-15

The murine PC-3 nucleotide sequence (SEQ ID NO: 1) and encoded amino acid sequence (SEQ ID NO: 2) are set forth in the Sequence listings herein. The coding sequence of the mature murine PC-3 protein begins at nucleotide #634 and continues through nucleotide #1008. Purified murine PC-3 proteins of the present invention are produced by culturing a host cell transformed with a DNA sequence comprising the DNA coding sequence of SEQ ID NO: 1 from nucleotide #634 to #1008, or from nucleotide #490 to #1008, and recovering and purifying from the culture medium a protein which contains the amino acid sequence or a substantially homologous sequence as represented by amino acids #-48 to #125 or #1 to #125 of SEQ ID NO: 2.

The human BMP-15 sequence of the present invention is obtained using the whole or fragments of the murine PC-3 DNA sequence, or a partial human BMP-15 sequence, as a probe. Thus, the human BMP-15 DNA sequence comprise the DNA sequence of nucleotides #1002 to #1376 of SEQ ID NO: 3. This sequence of the human BMP-15 DNA sequence corresponds well to nucleotides #634 to #1008 of the murine PC-3 DNA sequence shown in SEQ ID NO: 1. The human BMP-15 protein comprises the sequence of amino acids #1 to #125 of SEQ ID NO: 4.

It is expected that BMP-15 protein, as expressed by mammalian cells such as CHO cells, exists as a heterogeneous population of active species of BMP-15 protein with varying N-termini. It is expected that active species will comprise an amino acid sequence beginning with the cysteine residue at amino acid #24 of SEQ ID NO:4, or will comprise additional amino acid sequence further in the N-terminal direction. Thus, it is expected that DNA sequences encoding active BMP-15 proteins will comprise a nucleotide sequence comprising nucleotides #576, #813, #1002 or #1071 to #1373 or #1376 of SEQ ID NO: 3. Accordingly, active species of human BMP-15 are expected to include those comprising amino acids #-142, #-63, #1 or #24 to #124 or #125 of SEQ ID NO:4.

A host cell may be transformed with a coding sequence encoding a propeptide suitable for the secretion of proteins by the host cell is linked in proper reading frame to the coding sequence for the mature PC-3 or BMP-15 protein. For example, see U.S. Pat. No. 5,168,050, the disclosure of which is hereby incorporated by reference, in which a DNA encoding a precursor portion of a mammalian protein other than BMP-2 is fused to the DNA encoding a mature BMP-2 protein. See also the specification of co-pending patent application, Ser. No. 08/362,670, filed on Dec. 22, 1994, in which the propeptide of BMP-2 is fused to the DNA encoding a mature BMP-12 protein. The disclosure of both of these references are hereby incorporated by reference. Thus, the present invention includes chimeric DNA molecules comprising a DNA sequence encoding a propeptide from a member of the TGF-β superfamily of proteins, other than BMP-15, is linked in correct reading frame to a DNA sequence encoding a BMP-15-related protein, such as PC-3 or BMP-15 protein. The term "chimeric" is used to signify that the propeptide originates from a different polypeptide than the BMP-15-related protein.

The N-terminus of one active species of human BMP-15 is expected to be experimentally determined by expression in *E. coli* to be as follows: [M]QADGISAE. Thus, it appears that the N-terminus of this species of BMP-15 is at amino acid #1 of SEQ ID NO: 3, and a DNA sequence encoding said species of BMP-15 would comprise nucleotides #1002 to #1376 of SEQ ID NO: 3. The apparent molecular weight of human BMP-15 monomer is expected to be experimentally determined by SDS–PAGE to be approximately 10–17 kd on a Novex 16% tricine gel. The human BMP-15 protein is expected to exist as a clear, colorless solution in 0.1% trifluoroacetic acid.

It is expected that other BMP-15-related proteins, such as PC-3, as expressed by mammalian cells such as CHO cells, also exist as a heterogeneous population of active species of BMP-15-related protein with varying N-termini. For example, it is expected that active species of PC-3 will comprise an amino acid sequence beginning with the cysteine residue at amino acid #24 of SEQ ID NO:2, or will comprise additional amino acid sequence further in the N-terminal direction. Thus, it is expected that DNA sequences encoding active PC-3 proteins include those which comprise a nucleotide sequence comprising nucleotides #427, #490, #634, #640, #664 or #703 to #1005 or #1008 of SEQ ID NO: 1. Accordingly, active PC-3 proteins include those comprising amino acids #-69, #-48, #1, #3, #11 or #24 to #124 or #125.

The BMP-15-related proteins of the present invention, include polypeptides having a molecular weight of about 10–17 kd in monomeric form, said polypeptide comprising the amino acid sequence of SEQ ID NO:10 and having the ability to induce the formation of cartilage and/or bone and/or other connective tissue in the Rosen-Modified Sampath-Reddi ectopic implant assay, described in the examples.

The BMP-15-related proteins recovered from the culture medium are purified by isolating them from other proteinaceous materials from which they are co-produced and from other contaminants present. BMP-15-related proteins may be characterized by the ability to induce the formation of cartilage and/or bone and/or other connective tissue, for example, in the rat bone formation assay described below.

The BMP-15-related proteins provided herein also include factors encoded by the sequences similar to those of SEQ ID NO: 1 or SEQ ID NO:3, but into which modifications are naturally provided (e.g. allelic variations in the nucleotide sequence which may result in amino acid changes in the polypeptide) or deliberately engineered. For example, synthetic polypeptides may wholly or partially duplicate continuous sequences of the amino acid residues of SEQ ID NO:2 or SEQ ID NO:4. These sequences, by virtue of sharing primary, secondary, or tertiary structural and conformational characteristics with bone growth factor polypeptides of SEQ ID NO: 2 or SEQ ID NO: 4 may possess bone growth factor biological properties in common therewith. Thus, they may be employed as biologically active substitutes for naturally-occurring BMP-15 and other BMP-15-related polypeptides in therapeutic processes.

Other specific mutations of the sequences of BMP-15-related proteins described herein involve modifications of glycosylation sites. These modifications may involve O-linked or N-linked glycosylation sites. For instance, the absence of glycosylation or only partial glycosylation results from amino acid substitution or deletion at asparagine-linked glycosylation recognition sites. The asparagine-linked glycosylation recognition sites comprise tripeptide sequences which are specifically recognized by appropriate cellular glycosylation enzymes. These tripeptide sequences are either asparagine-X-threonine or asparagine-X-serine, where X is usually any amino acid. A variety of amino acid substitutions or deletions at one or both of the first or third amino acid positions of a glycosylation recognition site (and/or amino acid deletion at the second position) results in non-glycosylation at the modified tripeptide sequence. Additionally, bacterial expression of BMP-15-related protein will also result in production of a non-glycosylated protein, even if the glycosylation sites are left unmodified.

The present invention also encompasses the novel DNA sequences, free of association with DNA sequences encoding other proteinaceous materials, and coding for expression of BMP-15-related proteins. These DNA sequences include those depicted in SEQ ID NO: 1 and SEQ ID NO: 3 in a 5' to 3' direction and those sequences which hybridize thereto under stringent hybridization conditions [for example, 0.1× SSC, 0.1% SDS at 65° C.; see, T. *Maniatis et al, Molecular Cloning (A Laboratory Manual)*, Cold Spring Harbor Laboratory (1982), pages 387 to 389] and encode a protein having cartilage and/or bone and/or other connective tissue inducing activity. These DNA sequences also include those which comprise the DNA sequence of SEQ ID NO: 1 or SEQ ID NO: 3 and those which hybridize thereto under stringent hybridization conditions and encode a protein having cartilage and/or bone and/or other connective tissue inducing activity.

Similarly, DNA sequences which code for BMP-15-related proteins coded for by the sequences of SEQ ID NO: 1 or SEQ ID NO: 3, or BMP-15-related proteins which comprise the amino acid sequence of SEQ ID NO: 2 or SEQ ID NO: 4, but which differ in codon sequence due to the degeneracies of the genetic code or allelic variations (naturally-occurring base changes in the species population which may or may not result in an amino acid change) also encode the novel factors described herein. Variations in the DNA sequences of SEQ ID NO: 1 or SEQ ID NO: 3 which are caused by point mutations or by induced modifications (including insertion, deletion, and substitution) to enhance the activity, half-life or production of the polypeptides encoded are also encompassed in the invention.

Another aspect of the present invention provides a novel method for producing BMP-15-related proteins. The method of the present invention involves culturing a suitable cell line, which has been transformed with a DNA sequence encoding a BMP-15-related protein of the invention, under the control of known regulatory sequences. The transformed host cells are cultured and the BMP-15-related proteins recovered and purified from the culture medium. The purified proteins are substantially free from other proteins with which they are co-produced as well as from other contaminants.

Suitable cells or cell lines may be mammalian cells, such as Chinese hamster ovary cells (CHO). The selection of suitable mammalian host cells and methods for transformation, culture, amplification, screening, product production and purification are known in the art. See, e.g., Gething and Sambrook, *Nature*, 293:620–625 (1981), or alternatively, Kaufman et al, *Mol. Cell. Biol.*, 5(7): 1750–1759 (1985) or Howley et al, U.S. Pat. No. 4,419,446. Another suitable mammalian cell line, which is described in the accompanying examples, is the monkey COS-1 cell line. The mammalian cell CV-1 may also be suitable.

Bacterial cells may also be suitable hosts. For example, the various strains of *E. coli* (e.g., HB101, MC1061) are well-known as host cells in the field of biotechnology. Various strains of *B. subtilis*, Pseudomonas, other bacilli and the like may also be employed in this method. For expression of the protein in bacterial cells, DNA encoding the propeptide of BMP-15-related is generally not necessary.

Many strains of yeast cells known to those skilled in the art may also be available as host cells for expression of the polypeptides of the present invention. Additionally, where desired, insect cells may be utilized as host cells in the method of the present invention. See, e.g. Miller et al, *Genetic Engineering*, 8:277–298 (Plenum Press 1986) and references cited therein.

Another aspect of the present invention provides vectors for use in the method of expression of these novel BMP-15-related polypeptides. Preferably the vectors contain the full novel DNA sequences described above which encode the novel factors of the invention. Additionally, the vectors contain appropriate expression control sequences permitting expression of the BMP-15-related protein sequences. Alternatively, vectors incorporating modified sequences as described above are also embodiments of the present invention. Additionally, the sequence of SEQ ID NO:1, SEQ ID NO:3 or other sequences encoding BMP-15-related proteins could be manipulated to express a mature BMP-15-related protein by deleting BMP-15-related propeptide sequences and replacing them with sequences encoding the complete propeptides of other BMP proteins or members of the TGF-β superfamily. Thus, the present invention includes chimeric DNA molecules encoding a propeptide from a member of the TGF-fi superfamily linked in correct reading frame to a DNA sequence encoding a BMP-15-related polypeptide.

The vectors may be employed in the method of transforming cell lines and contain selected regulatory sequences in operative association with the DNA coding sequences of the invention which are capable of directing the replication and expression thereof in selected host cells. Regulatory sequences for such vectors are known to those skilled in the art and may be selected depending upon the host cells. Such selection is routine and does not form part of the present invention.

A protein of the present invention, which induces cartilage and/or bone and/or other connective tissue formation in circumstances where such tissue is not normally formed, has application in the healing of bone fractures and cartilage or other connective tissue defects in humans and other animals. Such a preparation employing a BMP-15-related protein may have prophylactic use in closed as well as open fracture reduction and also in the improved fixation of artificial joints. De novo bone formation induced by an osteogenic agent contributes to the repair of congenital, trauma induced, or oncologic resection induced craniofacial defects, and also is useful in cosmetic plastic surgery. A BMP-15-related protein may be used in the treatment of periodontal disease, and in other tooth repair processes. Such agents may provide an environment to attract bone-forming cells, stimulate growth of bone-forming cells or induce differentiation of progenitors of bone-forming cells, and may also support the regeneration of the periodontal ligament and attachment apparatus, which connects bone and teeth. BMP-15-related polypeptides of the invention may also be useful in the treatment of osteoporosis. A variety of osteogenic, cartilage-inducing and bone inducing factors have been described. See, e.g., European patent applications 148,155 and 169,016 for discussions thereof.

The proteins of the invention may also be used in wound healing and related tissue repair. The types of wounds include, but are not limited to burns, incisions and ulcers. (See, e.g. PCT Publication WO84/01106 for discussion of wound healing and related tissue repair). It is further contemplated that proteins of the invention may increase neuronal survival and therefore be useful in transplantation and treatment of conditions exhibiting a decrease in neuronal survival. The proteins of the invention may further be useful for the treatment of conditions related to other types of tissue, such as epidermis and muscle.

A further aspect of the invention is a therapeutic method and composition for repairing fractures and other conditions related to cartilage and/or bone and/or other connective tissue defects or periodontal diseases. The invention further comprises therapeutic methods and compositions for wound healing and tissue repair. Such compositions comprise a therapeutically effective amount of at least one of the BMP-15-related proteins of the invention in admixture with a pharmaceutically acceptable vehicle, carrier or matrix. It is further contemplated that compositions of the invention may increase neuronal survival and therefore be useful in transplantation and treatment of conditions exhibiting a decrease in neuronal survival. Compositions of the invention may further include at least one other therapeutically useful agent, such as members of the TGF-β superfamily of proteins, which includes the BMP proteins BMP-1, BMP-2, BMP-3, BMP-4, BMP-5, BMP-6 and BMP-7, disclosed for instance in U.S. Pat. Nos. 5,108,922; 5,013,649; 5,116,738; 5,106,748; 5,187,076; and 5,141,905; BMP-8, disclosed in PCT publication WO91/18098; BMP-9, disclosed in PCT publication WO93/00432; BMP-10, disclosed in PCT application WO94/26893; BMP-11, disclosed in PCT application WO94/26892, or BMP-12 or BMP-13, disclosed in co-pending patent application, Ser. No. 08/362,670, filed on Dec. 22, 1994. Other compositions which may also be useful include Vgr-2, and any of the GDFs, including those described in PCT applications WO94/15965; WO94/15949; WO95/01801; WO95/01802; WO94/21681; WO94/15966; and others. Also useful in the present invention may be BIP, disclosed in WO94/01557; and MP52, disclosed in PCT application WO93/16099. The disclosures of the above applications are hereby incorporated by reference herein.

It is expected that BMP-15 and BMP-15-related proteins may exist in nature as homodimers or heterodimers. To promote the formation of dimers of BMP-15 and BMP-15-related proteins with increased stability, one can genetically engineer the DNA sequence of SEQUENCE ID NO:1 or SEQUENCE ID NO:3 to provide one or more additional cysteine residues to increase potential dimer formation. The resulting DNA sequence would be capable of producing a "cysteine added variant" of BMP-15 or a BMP-15 related protein. In a preferred embodiment, one would engineer the DNA sequence of SEQUENCE ID NO:3 so that the codon appearing at nucleotides #1266 to #1268 is altered to a nucleotide triplet encoding a cysteine residue, such as TGT or TGC. Similarly, one could alter the DNA sequence of SEQUENCE ID NO: 1 to replace the codon triplet at nucleotides #898 to #900 to a triplet encoding a cysteine residue, such as TGT or TGC. Alternatively, one can produce "cysteine added variants" of BMP-15 or BMP-15-related proteins by altering the sequence of the protein at the amino acid level, for example, by altering the amino acid sequences of SEQUENCE ID NO:2 or SEQUENCE ID NO:4 at amino acid residue #89 from Ser to Cys. Production of "cysteine added variants" of proteins is described in U.S. Pat. No. 5,166,322, the disclosure of which is hereby incorporated by reference.

It is expected that the proteins of the invention may act in concert with or perhaps synergistically with other related proteins and growth factors. Further therapeutic methods and compositions of the invention therefore comprise a therapeutic amount of at least one BMP-15-related protein of the invention with a therapeutic amount of at least one other member of the TGF-β superfamily of proteins, such as the BMP proteins disclosed in the applications described above. Such combinations may comprise separate molecules of the BMP proteins or heteromolecules comprised of different BMP moieties. For example, a method and composition of the invention may comprise a disulfide linked dimer comprising a BMP-15-related protein subunit and a subunit from one of the "BMP" proteins described above. Thus, the present invention includes a purified BMP-15-related polypeptide which is a heterodimer wherein one subunit comprises the amino acid sequence from amino acid #1 to amino acid #125 of SEQ ID NO:2 or amino acid #1 to #125 of SEQ ID NO:4, and one subunit comprises an amino acid sequence for a bone morphogenetic protein selected from the group consisting of BMP-1, BMP-2, BMP-3, BMP-4, BMP-5, BMP-6, BMP-7, BMP-8, BMP-9, BMP-10, BMP-11 or BMP-12 or BMP-13, disclosed in co-pending patent application, Ser. No. 08/362,670, filed on Dec. 22, 1994. A further embodiment may comprise a heterodimer of BMP-15-related moieties, for examples of human BMP-15 and the human homologue of murine PC-3. Further, BMP-15-related proteins may be combined with other agents ben the bone and/or cartilage and/or other connective tissue defect, wound, or tissue in question. These agents include various growth factors such as epidermal growth factor (EGF), fibroblast growth factor (FGF), platelet derived growth factor (PDGF), transforming growth factors (TGF-α and TGF-β), activins, inhibins, and k-fibroblast growth factor (kFGF), parathyroid hormone (PTH), leukemia inhibitory factor (LIF/HILDA/DIA), insulin-like growth factors (IGF-I and IGF-II). Portions of these agents may also be used in compositions of the present invention.

The preparation and formulation of such physiologically acceptable protein compositions, having due regard to pH, isotonicity, stability and the like, is within the skill of the art. The therapeutic compositions are also presently valuable for veterinary applications due to the lack of species specificity in BMP proteins. Particularly domestic animals and thoroughbred horses in addition to humans are desired patients for such treatment with the BMP-15-related proteins of the present invention.

The therapeutic method includes administering the composition topically, systemically, or locally as an implant or device. When administered, the therapeutic composition for use in this invention is, of course, in a pyrogen-free, physiologically acceptable form. Further, the composition may desirably be encapsulated or injected in a viscous form for delivery to the site of bone, cartilage or other connective tissue or other tissue damage. Topical administration may be suitable for wound healing and tissue repair. Therapeutically useful agents other than the BMP-15-related proteins which may also optionally be included in the composition as described above, may alternatively or additionally, be administered simultaneously or sequentially with the BMP composition in the methods of the invention.

Preferably for bone and/or cartilage and/or other connective tissue formation, the composition includes a matrix capable of delivering BMP-15-related or other BMP proteins to the site of bone and/or cartilage and/or other connective tissue damage, providing a structure for the developing bone and cartilage and other connective tissue and optimally capable of being resorbed into the body. The matrix may provide slow release of BMP-15-related and/or other bone inductive protein, as well as proper presentation and appropriate environment for cellular infiltration. Such matrices may be formed of materials presently in use for other implanted medical applications.

The choice of matrix material is based on biocompatibility, biodegradability, mechanical properties, cosmetic appearance and interface properties. The particular application of the BMP-15-related compositions will define the appropriate formulation. Potential matrices for the compositions may be biodegradable and chemically defined calcium sulfate, tricalciumphosphate, hydroxyapatite, polylactic acid and polyanhydrides. Other potential materials are biodegradable and biologically well defined, such as bone or derreal collagen. Further matrices are comprised of pure proteins or extracellular matrix components. Other potential matrices are nonbiodegradable and chemically defined, such as sintered hydroxyapatite, bioglass, aluminates, or other ceramics. Matrices may be comprised of combinations of any of the above mentioned types of material, such as polylactic acid and hydroxyapatite or collagen and tricalciumphosphate. The bioceramics may be altered in composition, such as in calcium-aluminate-phosphate and processing to alter pore size, particle size, particle shape, and biodegradability.

The dosage regimen will be determined by the attending physician considering various factors which modify the action of the BMP-15-related protein, e.g. amount of bone weight desired to be formed, the site of bone damage, the condition of the damaged bone, the size of a wound, type of damaged tissue, the patient's age, sex, and diet, the severity of any infection, time of administration and other clinical factors. The dosage may vary with the type of matrix used in the reconstitution and the types of BMP proteins in the composition. The addition of other known growth factors, such as IGF I (insulin like growth factor I), to the final composition, may also effect the dosage.

Progress can be monitored by periodic assessment of bone growth and/or repair. The progress can be monitored, for example, x-rays, histomorphometric determinations and tetracycline labeling.

The following examples illustrate practice of the present invention in recovering and characterizing murine PC-3 protein and employing the DNA it to recover human BMP-15 and other BMP-15-related proteins, obtaining the human proteins and expressing the proteins via recombinant techniques.

EXAMPLES

Example 1

Isolation of DNA

DNA sequences encoding BMP-15 and BMP-15 related proteins, such as the murine PC-3 protein may be isolated by various techniques known to those skilled in the art. As described below, oligonucleotide primers may be designed on the basis of amino acid sequences present in other BMP proteins, Vg-1 related proteins and other promins of the TGF-β superfamily. Regions containing amino acid sequences which are highly conserved within the BMP family of proteins and within other members of the TGF-β superfamily of proteins can be identified and consensus amino acid sequences of these highly conserved regions can be constructed based on the similarity of the corresponding regions of individual BMP/TGF-β/Vg-1 promins. An example of such a consensus amino acid sequence is indicated below. Consensus amino acid sequence (1):

Trp-Gln/Asn/Asp-Asp/Glu/Asn-Trp-Ile-Val/Ile-Ala (SEQ ID NO:#5 )

Where X/Y indicates that either amino acid residue may appear at that position.

The following oligonucleotide is designed on the basis of the above identified consensus amino acid sequence (1):

GCGGATCCTGGVANGABTGGATHRTNGC (SEQ ID NO:#6) #1

This oligonucleotide sequence is synthesized on an automated DNA synthesizer. The standard nucleotide symbols in the above identified oligonucleotide primer are as follows: A,adenosine; C,cytosine; G,guanine; T,thymine; N,adenosine or cytosine or guanine or thymine; R,adenosine or cytosine; Y,cytosine or thymine; H,adenosine or cytosine or thymine; V,adenosine or cytosine or guanine; D,adenosine or guanine or thymine.

The first eight nucleotides of oligonucleotide #1 (underlined) contain the recognition sequence for the restriction endonuclease BamHI in order to facilitate the manipulation of a specifically amplified DNA sequence encoding the PC-3 protein and are thus not derived from the consensus amino acid sequence (1) presented above.

A second consensus amino acid sequence is derived from another highly conserved region of BMP/TGF-β/Vg-1 proteins as described below:

Asn-His-Ala-Ile-Val/Leu-Gln-Thr (SEQ ID NO: #7)

The following oligonucleotide is designed on the basis of the above identified consensus amino acid sequence (2):

GCTCTAGAGTYTGNAYNATNGCRTGRTT (SEQ ID NO: 8) #2

This oligonucleotide sequence is synthesized on an automated DNA synthesizer. The same nucleotide symbols are used as described above.

The first eight nucleotides of oligonucleotide #2 (underlined) contain the recognition sequence for the restriction endonuclease XbaI in order to facilitate the manipulation of a specifically amplified DNA sequence encoding the PC-3 protein and are thus not derived from the consensus amino acid sequence (2) presented above.

It is contemplated that the PC-3 protein of the invention and other BMP/TGF-β/3/Vg-1 related proteins may contain amino acid sequences similar to the consensus amino acid sequences described above and that the location of those sequences within a BMP-15 or PC-3 protein or other novel related proteins would correspond to the relative locations in the proteins from which they were derived. It is further contemplated that this positional information derived from the structure of other BMP/TGF-β/Vg-1 proteins and the oligonucleotide sequences #1 and #2 which have been derived from consensus amino acid sequences (1) and (2), respectively, could be utilized to specifically amplify DNA sequences encoding the corresponding amino acids of a BMP-15 protein or other BMP/TGF-β/Vg-1 related proteins.

Based on the knowledge of the gene structures of BMP/TGF-β/Vg-1 proteins, it is further contemplated that human or murine genomic DNA can be used as a template to perform specific amplification reactions which would result in the identification of BMP-15 BMP/TGF-β/1 Vg-1 (BMP-15 related protein) encoding sequences. Such specific amplification reactions of a human or murine genomic DNA template could be initiated with the use of oligonucleotide primers #1 and #2 described earlier. Oligonucleotides #1 and #2 identified above are utilized as primers to allow the specific amplification of a specific nucleotide sequence from murine genomic DNA. The amplification reaction is performed as follows:

Murine genomic DNA is sheared by repeated passage through a 25 gauge needle, denatured at 100° C. for 5 minutes and then chilled on ice before adding to a reaction mixture containing 200/μM each deoxynucleotide triphosphates (dATP, dGTP, dCTP and dTTP), 10 mM Tris-HCl pH 8.3, 50 mM KCl, 1.5 mM $MgCl_2$, 0.001% gelatin, 1.25 units Taq DNA polymerase, 50 pM oligonucleotide #1 and 50 pM oligonucleotide #2, in a total reaction volume of 50/μl. This reaction mixture is subjected to thermal cycling in the following manner: 1 minute at 94° C., 1 minute at 37° C., 2 minutes at 72° C. for thirty cycles; followed by a 7 minute incubation at 72° C.

The DNA which is specifically amplified by this reaction is ethanol precipitated, digested with the restriction endonucleases BamHI and XbaI and subjected to agarose gel electrophoresis. A region of the gel, corresponding to the predicted size of the BMP-15 or other BMP/TGFβ/Vg-1 encoding DNA fragment, is excised and the specifically amplified DNA fragments contained therein are electroeluted and subcloned into the plasmid vector pGEM-3 between the XbaI and BamHI sites of the polylinker. DNA sequence analysis of one of the resulting BMP-15 related subclones indicates the specifically amplified DNA sequence product contained therein encodes a portion of the BMP-15-related protein, mPC-3, of the invention.

The DNA sequence (SEQ ID NO:9) and derived amino acid sequence (SEQ ID NO: 10) of this specifically amplified DNA fragment of mPC-3 are shown in the SEQUENCE Listings.

Nucleotides #1–#26 of SEQ ID NO:9 comprise a portion of oligonucleotide #1 and nucleotides #100–#3119 comprise a portion of the reverse compliment of oligonucleotide #2 utilized to perform the specific amplification reaction. Due to the function of oligonucleotides #1 and #2 in initiating the amplification reaction, they may not correspond exactly to the actual sequence encoding a PC-3 protein and are therefore not translated in the corresponding amino acid derivation (SEQ ID NO:10).

The following oligonucleotide probes are designed on the basis of the specifically amplified PC-3 murine DNA sequence set forth above (SEQ ID NO:9) and synthesized on an automated DNA synthesizer:

TCCTCGTCTCTATACCCCAAATTACTG-
    TAAAGGAATCTGT(SEQ ID NO:11)        #3 and

ATCTGTACTCGGGTATTACCCTATGGTCTCAATTCACCC
    (SEQ ID NO:#12)        #4

Oligonucleotide probes #3 and #4 are designed on the basis of nucleotides #27–#66 and #61–#99 of the murine PC-3 sequence set forth in SEQ ID NO: 9.

These oligonucleotide probes are radioactively labeled with $^{32}$P and employed to screen a murine genomic library constructed in the vector λFIX II (Stratagene catalog #946309). 500,000 recombinants of the human genomic library are plated at a density of approximately 10,000 recombinants per plate on 50 plates. Duplicate nitrocellulose replicas of the recombinant bacteriophage plaques are made one set of nitrocellulose filters is hybridized to oligonucleotide probe #3 and the duplicate set of nitrocellulose filters is hybridized to oligonucleotide #4, both in a hybridization buffer consisting of 5×SSC, 1% SDS, 10% dextran sulfate, 2×Denhardt's, 100 μ/ml herring sperm DNA) at 60° C. overnight. The following day the radioactively labelled oligonucleotide containing hybridization solution is removed an the filters are washed with 5×SSC, 0.1% SDS at 60° C. Two recombinants which hybridize to both oligonucleotide probes are identified and one is plaque purified. This plaque purified recombinant bacteriophage clone which hybridizes to the murine PC-3 oligonucleotide probes #3 and #4 is designated Ø60. A bacteriophage plate stock is made and bacteriophage DNA is isolated from the Ø60 murine genomic clone. The complete insert of the Ø60 murine genomic recombinant is excised with the restriction endonuclease NotI, subcloned into a plasmid vector (pBluescript) and DNA sequence analysis is performed. This plasmid subclone is designated mPC-3/NotI-18 and has been deposited with the American Type Cultu Parklawn Drive, Rockville, Md. "ATCC" under the accession #69777 on Mar. 30, 1995. This deposit meets the requirements of the Budapest Treaty of the International Recognition of the Deposit of Microorganisms for the Purpose of Patent Procedure and Regulations thereunder.

The partial DNA sequence (SEQ ID NO:1) and derived amino acid sequence (SEQ ID NO:2) of the approximately 18 kb DNA insert of the plasmid subclone mPC-3/NotI-18, derived from clone Ø60, are shown in the Sequence Listings.

It should be noted that nucleotides #765–#837 of SEQ ID NO:1 correspond to nucleotides #28–#99 of the specifically amplified murine PC-3 encoding DNA fragment set forth in SEQ ID NO:9 thus confirming that the murine genomic bacteriophage clone Ø60 and derivative subclone mPC-3/NotI-18 encode at least a portion of the PC-3 protein of the invention. The nucleotide sequence of a portion of the 18 kb NotI insert of the plasmid mPC-3/NotI-18 contains an open reading frame of 885 base pairs, as defined by nucleotides #124–#1008 of SEQ ID NO: 1.

The 5' limit of this open reading frame is defined by a stop codon at nucleotide positions #121–#123. As this sequence is derived from a genomic clone it is difficult to determine the boundary between the 5' extent of coding sequence and the 3' limit of intervening sequence (intron/non-coding sequence), however, nucleotides #127–#154 are predicted to represent sequences characteristic of a splice acceptor site, including the invariant dinucleotide AG found at positions #153–#154, which delineate the 3' limit of an intron in genomic sequences. This predicts the 5' boundary of a single exon which encodes the entire mature peptide and a substantial portion of the propeptide of the murine PC-3 protein of the invention. The 852 base pair open reading frame of this predicted exon (nucleotides #157–#1008 of SEQ ID NO:1) encodes at least 284 amino acids of the murine PC-3 protein of the invention. The encoded 284 amino acid murine PC-3 protein includes the full mature murine PC-3 peptide (amino acids #1–#125 of SEQ ID NO:2), as well as the C-terminal portion of the propeptide region of the primary translation product (amino acid #-159 to #-1 of SEQ ID NO:2).

Based on the knowledge of other BMP proteins and other proteins within the TGF-β family, it is predicted that the precursor polypeptide would be cleaved at the multibasic sequence Arg-Ser-Val-Arg in agreement with a proposed consensus proteolytic processing sequence of Arg-X-X-Arg. Cleavage of the murine PC-3 precursor polypeptide is expected to generate a 125 amino acid mature peptide beginning with the amino acid Gln at position #1 of SEQ ID NO:2. The processing of murine PC-3 into the mature form is expected to involve dimerization and removal of the N-terminal region in a manner analogous to the processing of the related protein TGF-β[Gentry et al., *Molec & Cell. Biol.*, 8:4162 (1988); Derynck et al. *Nature*, 316:701 (1985)].

It is contemplated therefore that the mature active species of murine PC-3 comprises a homodimer of two polypeptide subunits, each subunit comprising amino acids #1 to #125 of SEQ ID NO:1 with a predicted molecular weight of approximately 14,000 daltons. Further active species are contemplated comprising at least amino acids #24 to #125 of SEQ ID NO:2, thereby including the first conserved cysteine residue.

As with other members of the TGF-β/BMP family of proteins, the carboxy-terminal portion of the murine PC-3 protein exhibits greater sequence conservation than the more amino-terminal portion. The percent amino acid identity of the murine PC-3 protein in the cysteine-rich C-terminal domain (amino acids#24–#125) to the corresponding region of human BMP proteins and other proteins within the TGF-β family is as follows: BMP-2, 42%; BMP-3, 39%; BMP-4, 41%; BMP-5, 39%; BMP-6, 40%; BMP-7, 38%; BMP-8, 35%; BMP-9, 38%; BMP-10, 40%; BMP-11, 33%; Vg1, 39%; GDF-1, 32%; TGF-β1, 26%; TGF-β2, 30%; TGF-β3, 29%; inhibin β(B), 30%; inhibin α(A), 34%.

The murine PC-3 DNA sequence (SEQ ID NO:1), or a portion thereof, can be used as a probe to identify a human cell line or tissue which synthesizes PC-3 or PC-3-related mRNA. Briefly described, RNA is extracted from a selected cell or tissue source and either electrophoresed on a form- aldehyde agarose gel and transferred to nitrocellulose, or reacted with formaldehyde and spotted on nitrocellulose directly. The nitrocellulose is then hybridized to a probe derived from the coding sequence of murine PC-3.

Alternatively, the murine PC-3 sequence is used to design oligonucleotide primers which will specifically amplify a portion of the PC-3 or PC-3-related encoding sequence located in the region between the primers utilized to perform the specific amplification reaction. It is contemplated that these murine PC-3 derived primers would allow one to specifically amplify corresponding human PC-3 or PC-3-related encoding sequences from mRNA, cDNA o templates. Once a positive source has been identified by one of the above described methods, mRNA is selected by oligo (dT) cellulose chromatography and cDNA is synthesized and cloned in λgt10 or other λ bacteriophage vectors known to those skilled in the art, for example,λZAP by established techniques (Toole et at., supra). It is also possible to perform the oligonucleotide primer directed amplification reaction, described above, directly on a pre-established human cDNA or genomic library which has been cloned into a λ bacteriophage vector. In such cases, a library which yields a specifically amplified DNA product encoding a portion of the human PC-3 or PC-3-related protein could be screened directly, utilizing the fragment of amplified human PC-3 or PC-3-related protein encoding DNA as a probe.

Oligonucleotide primers designed on the basis of the DNA sequence of the murine PC-3 genomic clone Ø60 are predicted to allow the specific amplification of human PC-3 or PC-3-related encoding DNA sequences from pre-established human cDNA libraries which are commercially available (i.e., Stratagene, La Jolla, Calif. or Clonetech Laboratories, Inc., Palo Alto, Calif.). The following oligonucleotide primer is designed on the basis of nucleotides #728 to #747 of the DNA sequence set forth in SEQ ID NO:1 and synthesized on an automated DNA synthesizer:

GCTTCCACCAACTAGGCTGG (SEQ ID NO:13)    #5

The following oligonucleotide primer is designed on the basis of the reverse compliment of nucleotides #1007–#988 of the DNA sequence set forth in SEQ ID NO:1 and synthesized on an automated DNA synthesizer:

CTACATGTACAGGACTGGGC (SEQ ID NO:14)    #6

The standard nucleotide symbols in the above identified primers are as follows: A, adenine; C, cytosine; G, guanine; T, thymine.

Primers #5 and #6 identified above are utilized as primers to allow the amplification of a specific PC-3 or PC-3-related encoding nucleotide sequence from pre-established cDNA libraries.

Approximately $1 \times 10^8$ pfu (plaque forming units) of λbacteriophage libraries containing human cDNA inserts such as those detailed above are denatured at 95° C. for five minutes prior to addition to a reaction mixture containing 200 µM each deoxynucleotide triphosphates (dATP, dGTP, dCTP and dTTP) 10 mM Tris-HCl pH 8.3, 50 mM KCl, 1.5 mM $MgCl_2$, 0.001% gelatin, 1.25 units Taq DNA polymerase, 100 pM oligonucleotide primer #4 and 100 pM oligonucleotide primer #5. The reaction mixture is then subjected to thermal cycling in the following manner: 1 minute at 94° C., 1 minute at 50° C., 1 minute at 72° C. for thirty-nine cycles followed by 10 minutes at 72° C.

The DNA which is specifically amplified by this reaction would be expected to generate a PC-3 or PC-3-related protein-encoding product of approximately 280 base pairs. The resulting 280 bp DNA product is visualized following electrophoresis of the reaction products through a 2 % agarose gel. Once a positive cDNA source has been identified in this manner, the corresponding cDNA library from which a PC-3 specific or PC-3-related sequence was amplified could be screened directly with the 280 bp insert or other PC-3 specific probes in order to identify and isolate cDNA clones encoding the full-length PC-3 or PC-3-related protein of the invention.

Additional methods known to those skilled in the art may be used to isolate other full-length cDNAs encoding human PC-3 related proteins, or full length cDNA clones encoding PC-3 related proteins of the invention from species other than humans, particularly other mammalian species.

Alternatively, oligonucleotides #5 and #6 described above (SEQ ID NO:13 and SEQ ID NO:14) are utilized as primers to allow the specific amplification of murine PC-3 specific nucleotide sequences from murine PC-3 encoding plasmid mPC-3/NotI-18. The amplification reaction is performed as follows: Approximately 25 ng of mPC-3/NotI-18 plasmid DNA is added to a reaction mixture containing 200 µM each deoxynucleotide triphosphates (dATP, dGTP, dCTP and dTTP) 10 mM Tris-HCl pH 8.3, 50 mM KCl, 1.5 mM $MgCl_2$, 0.001% gelatin, 1.25 units Taq DNA polymerase, 100 pM oligonucleotide primer #5 and 100 pM oligonucleotide primer #6. The reaction mixture is then subjected to thermal cycling in the following manner: 1 minute at 94° C, 1 minute at 53° C., 1 minute at 72° C. for thirty cycles.

The DNA which is specifically amplified by this reaction would be expected to generate a PC-3 or PC-3-related encoding product of approximately 280 base pairs. The resulting 280 bp DNA product is visualized following electrophoresis of the reaction products through a 2% agarose gel. The region of the gel containing the 280 base pair murine PC-3 DNA fragment is excised and the specifically amplified DNA fragments contained therein are extracted (by electroelution or by other methods known to those skilled in the art). The gel-extracted 280 base pair DNA amplification product was radioactively labelled with 32p and employed to screen a human genomic library constructed in the vector λ DASH II (Stratagene catalog #945203).

Human BMP-15

One million recombinants of the human genomic library are plated at a density of approximately 20,000 recombinants per plate on 50 plates. Duplicate nitrocellulose replicas of the recombinant bacteriophage plaques are hybridized, under reduced stringency conditions, to the specifically amplified 280 bp probe in standard hybridization buffer (SHB=5×SSC, 0.1% SDS, 5×Denhardt's, 100 µ/ml salmon sperm DNA) at 60° C. overnight. The following day the radioactively labelled oligonucleotide containing hybridization solution is removed an the filters are washed, under reduced stringency conditions, with 2×SSC, 0.1% SDS at 60° C. Multiple positively hybridizing recombinants are identified and plaque purified. One of the recombinant bacteriophage clones which hybridizes to the 280 base pair mPC-3 probe is designated λJLDc19. This recombinant bacteriophage clone is plaque purified, a bacteriophage plate stock is made and bacteriophage DNA is isolated from the λJLDc19 human genomic clone. The bacteriophage λJLDc19 has been deposited with the American Type Culture Collection, 12301 Parklawn Drive, Rockville, Md. "ATCC" under the accession #97106 on Mar. 30, 1995. This deposit meets the requirements of the Budapest Treaty of the International Recognition of the Deposit of Microorganisms for the Purpose of Patent Procedure and Regulations thereunder.

The hybridizing region of this recombinant, λJLDc19, is localized to a 3 kb Eco RI fragment. This fragment is subcloned into a plasmid vector (pGEM-3) and DNA sequence analysis is performed. This plasmid subclone is designated pGEMJLDc19/3.0 and has been deposited with the American Type Culture Collection, 12301 Parklawn Drive, Rockville, Md. "ATCC" under the accession 69779 on Mar. 30, 1995. This deposit meets the requirements of the Budapest Treaty of the International Recognition of the Deposit of Microorganisms for the Purpose of Patent Procedure and Regulations thereunder.

The partial DNA sequence (SEQ ID NO:3) and derived amino acid sequence (SEQ ID NO:4) of a portion of the 3.0 kb DNA insert of the plasmid subclone pGEMJLDc19/3.0, derived from clone λJLDc19, are shown in the Sequence Listings The DNA sequence of a portion of the 3.0 kb EcoRI insert of the plasmid pGEMJLDc19/3.0 is set forth in SEQ ID NO:3. contains an contains an open reading frame of 888 base pairs, as defined by nucleotides #489–90 1376 of SEQ ID NO:4.

The 5' limit of this open reading frame is defined by a stop codon at nucleotide positions #486–#488. As this sequence is derived from a genomic clone it is difficult to determine the boundary between the 5' extent of coding sequence and the 3' limit of intervening sequence (intron/non-coding sequence), however, nucleotides #498–190 528 are predicted to represent sequences characteristic of a splice acceptor site, including the invariant dinucleotide AG found at positions #527–#528, which delineate the 3' limit of an intron in genomic sequences. This predicts the 5' boundary of a single exon which encodes the entire mature peptide and a substantial portion of the propeptide of the human PC-3-related protein of the invention, designated BMP-15. The 846 base pair open reading frame of this predicted exon (nucleotides #531–#1376 of SEQ ID NO:3) encodes at least 282 amino acids of the human BMP-15 protein of the invention. The encoded 282 amino acid human BMP-15 protein includes the full mature human BMP-15 peptide (amino acids #1–#125 of SEQ ID NO:4), as well as the C-terminal portion of the propeptide region of the primary translation product (amino acid #-157 to #-1 of SEQ ID NO:4).

Based on the knowledge of other BMP proteins and other proteins within the TGF-β family, it is predicted that the precursor polypeptide would be cleaved at the multibasic sequence Arg-Arg-Thr-Arg in agreement with a proposed consensus proteolytic processing sequence of Arg-X-X-Arg. Cleavage of the human BMP-15 precursor polypeptide is expected to generate a 125 amino acid mature peptide beginning with the amino acid Gln at position #1 of SEQ ID NO:4. The processing of human BMP-15 into the mature form is expected to involve dimerization and removal of the N-terminal region in a manner analogous to the processing of the related protein TGFβ[Gentry et al., *Molec & Cell. Biol.*, 8:4162 (1988); Derynck et al. *Nature*, 316:701 (1985)].

It is contemplated therefore that the mature active species of human BMP-15 comprises a homodimer of two polypeptide subunits, each sub amino acids #1 to #125 of SEQ ID NO:4 with a predicted molecular weight of approximately 14,000 daltons. Further active species are contemplated comprising at least amino acids #24 to #125 of SEQ ID NO:4, thereby including the first conserved cysteine residue. As with other members of the TGF-β/BMP family of proteins, the carboxy-terminal portion of the human BMP-15 protein exhibits greater sequence conservation than the more amino-terminal portion. The percent amino acid identity of the human BMP-15 protein in the cysteine-rich C-terminal domain (amino acids #24–#125) to the corresponding region of human BMP proteins and other proteins within the TGF-β family is as follows: BMP-2, 43%; BMP-3, 35%; BMP-4, 42%; BMP-5, 41%; BMP-6, 41%; BMP-7, 39%; BMP-8, 34%; BMP-9, 40%; BMP-10, 43%; BMP-11, 32%; Vgl, 39%; GDF-1, 35%; TGF-β1, 28%; TGF-β2, 30%; TGF-β3, 31%; inhibin α(B), 31%; inhibin α(A), 33%.

Example 2

W-20 BIOASSAYS

A. Description of W-20 cells

Use of the W-20 bone marrow stromal cells as an indicator cell line is based upon the conversion of these cells to osteoblast-like cells after treatment with a BMP protein [Thies et al, *Journal of Bone and Mineral Research*, 5:305 (1990); and Thies et al, *Endocrinology*, 130:1318 (1992)]. Specifically, W-20 cells are a clonal bone marrow stromal cell line derived from adult mice by researchers in the laboratory of Dr. D. Nathan, Children's Hospital, Boston, Mass. Treatment of W-20 cells with certain BMP proteins results in (1) increased alkaline phosphatase production, (2) induction of PTH stimulated cAMP, and (3) induction of osteocalcin synthesis by the cells. While (1) and (2) represent characteristics associated with the osteoblast phenotype, the ability to synthesize osteocalcin is a phenotypic property only displayed by mature osteoblasts. Furthermore, to date we have observed conversion of W-20 stromal cells to osteoblast-like cells only upon treatment with BMPs. In this manner, the in vitro activities displayed by BMP treated W-20 cells correlate with the in vivo bone forming activity known for BMPs.

Below two in vitro assays useful in comparison of BMP activities of novel osteoinductive molecules are described.

B. W-20 Alkaline Phosphatase Assay Protocol

W-20 cells are plated into 96 well tissue culture plates at a density of 10,000 cells per well in 200/µl of media (DME with 10% heat inactivated fetal calf serum, 2 mM glutamine and 100 Units/ml penicillin+100/λg/ml streptomycin. The cells are allowed to attach overnight in a 95 % air, 5 % $CO_2$ incubator at 37° C.

The 200/µl of media is removed from each well with a multichannel pipettor and replaced with an equal volume of test sample delivered in DME with 10% heat inactivated fetal calf serum, 2 mM glutamine and 1% penicillin-streptomycin. Test substances are assayed in triplicate.

The test samples and standards are allowed a 24 hour incubation period with the W-20 indicator cells. After the 24 hours, plates are removed from the 37° C. incubator and the test media are removed from the cells.

The W-20 cell layers are washed 3 times with 200/µl per well of calcium/magnesium free phosphate buffered saline and these washes are discarded.

50/µl of glass distilled water is added to each well and the assay plates are then placed on a dry ice/ethanol bath for quick freezing. Once frozen, the assay plates are removed from the dry ice/ethanol bath and thawed at 37° C. This step is repeated 2 more times for a total of 3 freeze-thaw procedures. Once complete, the membrane bound alkaline phosphatase is available for measurement.

50 µl of assay mix (50 mM glycine, 0.05 % Triton X-100, 4 mM $MgCl_2$, 5 mM p-nitrophenol phosphate, pH=10.3) is added to each assay well and the assay plates are then incubated for 30 minutes at 37° C. in a shaking waterbath at 60 oscillations per minute.

At the end of the 30 minute incubation, the reaction is stopped by adding 100/µl of 0.2N NaOH to each well and placing the assay plates on ice.

The spectrophotometric absorbance for each well is read at a wavelength of 405 nanometers. These values are then compared to known standards to give an estimate of the alkaline phosphatase activity in each sample. For example, using known amounts of p-nitrophenol phosphate, absorbance values are generated. This is shown in Table I.

TABLE I

Absorbance Values for Known Standards of P-Nitrophenol Phosphate

| P-nitrophenol phosphate umoles | Mean absorbance (404 nm) |
| --- | --- |
| 0.000 | 0 |
| 0.006 | 0.261 +/− .024 |
| 0.012 | 0.521 +/− .031 |
| 0.018 | 0.797 +/− .063 |
| 0.024 | 1.074 +/− .061 |
| 0.030 | 1.305 +/− .083 |

Absorbance values for known amounts of BMPs can be determined and converted to µmoles of p-nitrophenol phosphate cleaved per unit time as shown in Table II.

TABLE II

Alkaline Phosphatase Values for W-20 Cells Treating with BMP-2

| BMP-2 concentration ng/ml | Absorbance Reading 405 nmeters | umoles substrate per hour |
| --- | --- | --- |
| 0 | 0.645 | 0.024 |
| 1.56 | 0.696 | 0.026 |
| 3.12 | 0.765 | 0.029 |
| 6.25 | 0.923 | 0.036 |
| 12.50 | 1.121 | 0.044 |
| 25.0 | 1.457 | 0.058 |
| 50.0 | 1.662 | 0.067 |
| 100.0 | 1.977 | 0.080 |

These values are then used to compare the activities of known amounts of BMP-15 to BMP-2.

C. Osteocalcin RIA Protocol

W-20 cells are plated at $10^6$ cells per well in 24 well multiwell tissue culture dishes in 2 mls of DME containing 10% heat inactivated fetal calf serum, 2 mM glutamine. The cells are allowed to attach overnight in an atmosphere of 95% air 5% $CO_2$ at 37° C.

The next day the medium is changed to DME containing 10% fetal calf serum, 2 mM glutamine and the test substance in a total volume of 2 ml. Each test substance is administered to triplicate wells. The test substances are incubated with the W-20 cells for a total of 96 hours with replacement at 48 hours by the same test medias.

At the end of 96 hours, 50 µl of the test media is removed from each well and assayed for osteocalcin production using a radioimmunoassay for mouse osteocalcin. The details of the assay are described in the kit manufactured by Biomedical Technologies Inc., 378 Page Street, Stoughton, Mass. 02072. Reagents for the assay are found as product numbers BT-431 (mouse osteocalcin standard), BT-432 (Goat anti-mouse Osteocalcin), BT-431R (iodinated mouse osteocalcin), BT-415 (normal goat serum) and BT-414 (donkey anti goat IgG). The RIA for osteocalcin synthesized by W-20 cells in response to BMP treatment is carried out as described in the protocol provided by the manufacturer.

The values obtained for the test samples are compared to values for known standards of mouse osteocalcin and to the mount of osteocalcin produced by W-20 cells in response to challenge with known amounts of BMP-2. The values for BMP-2 induced osteocalcin synthesis by W-20 cells is shown in Table III.

TABLE III

Osteocalcin Synthesis by W-20 Cells

| BMP-2 Concentration ng/ml | Osteocalcin Synthesis ng/well |
| --- | --- |
| 0 | 0.8 |
| 2 | 0.9 |
| 4 | 0.8 |
| 8 | 2.2 |
| 16 | 2.7 |
| 31 | 3.2 |
| 62 | 5.1 |
| 125 | 6.5 |
| 250 | 8.2 |
| 500 | 9.4 |
| 1000 | 10.0 |

Example 3

ROSEN MODIFIED SAMPATH-REDDI ASSAY

A modified version of the rat bone formation assay described in Sampath and Reddi, *Proc. Natl. Acad. Sci. USA*, 80:6591–6595 (1983) is used to evaluate bone and/or cartilage and/or other connective tissue activity of BMP proteins. This modified assay is herein called the Rosen-modified Sampath-Reddi assay. The ethanol precipitation step of the Sampath-Reddi procedure is replaced by dialyzing (if the composition is a solution) or diafiltering (if the composition is a suspension) the fraction to be assayed against water. The solution or suspension is then equilibrated to 0.1% TFA. The resulting solution is added to 20 mg of rat matrix. A mock rat matrix sample not treated with the protein serves as a control. This material is frozen and lyophilized and the resulting powder enclosed in #5 gelatin capsules. The capsules are implanted subcutaneously in the abdominal thoracic area of 21–49 day old male Long Evans rats. The implants are removed after 7–14 days. Half of each implant is used for alkaline phosphatase analysis [see, Reddi et al, *Proc. Natl. Acad. Sci.*, 69:1601 (1972)].

The other half of each implant is fixed and processed for histological analysis. 1 µm glycolmethacrylate sections are stained with Von Kossa and acid fuschin to score the amount of induced bone and cartilage and other connective tissue formation present in each implant. The terms +1 through +5 represent the area of each histological section of an implant occupied by new bone and/or cartilage cells and matrix. A score of +5 indicates that greater than 50% of the implant is new bone and/or cartilage produced as a direct result of protein in the implant. A score of +4, +3, +2, and +1 would indicate that greater than 40%, 30%, 20% and 10% respectively of the implant contains new cartilage and/or bone.

Alternatively, the implants are inspected for the appearance of tissue resembling embryonic tendon, which is easily recognized by the presence of dense bundles of fibroblasts oriented in the same plane and packed tightly together. [Tendon/ligament-like tissue is described, for example, in Ham and Cormack, *Histology*(JB Lippincott Co. (1979), pp. 367–369, the disclosure of which is hereby incorporated by reference]. These findings may be reproduced in additional assays in which tendon/ligament-like tissues are observed in the BMP-15-related protein containing implants.

The BMP-15-related proteins of this invention may be assessed for activity on this assay.

Example 4

Expression of BMP-15

In order to produce murine, human or other mammalian BMP-15-related proteins, the DNA encoding it is transferred into an appropriate expression vector and introduced into mammalian cells or other preferred eukaryotic or prokaryotic hosts by conventional genetic engineering techniques. The preferred expression system for biologically active recombinant human BMP-15 is contemplated to be stably transformed mammalian cells.

One skilled in the art can construct mammalian expression vectors by employing the sequence of SEQ ID NO: 1 or SEQ ID NO: 3, or other DNA sequences encoding BMP-15-related proteins or other modified sequences and known vectors, such as pCD [Okayama et al., *Mol. Cell Biol.*, 2:161–170 (1982)], pJL3, pJL4 [Gough et al., *EMBO J*, 4:645–653 (1985)]and pMT2 CXM.

The mammalian expression vector pMT2 CXM is a derivative of p91023(b) (Wong et al., Science 228:810–815, 1985) differing from the latter in that it contains the ampicillin resistance gene in place of the tetracycline resistance gene and further contains a XhoI site for insertion of cDNA clones. The functional elements of pMT2 CXM have been described (Kaufman, R. J., 1985, Proc. Natl. Acad. Sci. U.S.A. 82:689–693) and include the adenovirus VA genes, the SV40 origin of replication including the 72 bp enhancer, the adenovirus major late promoter including a 5' splice site and the majority of the adenovirus tripartite leader sequence present on adenovirus late mRNAs, a 3' splice acceptor site, a DHFR insert, the SV40 early polyadenylation site (SV40), and pBR322 sequences needed for propagation in *E. coli*.

Plasmid pMT2 CXM is obtained by EcoRI digestion of pMT2-VWF, which has been deposited with the American Type Culture Collection (ATCC), Rockville, Md. (U.S.A.) under accession number ATCC 67122. EcoRI digestion excises the cDNA insert present in pMT2-VWF, yielding pMT2 in linear form which can be ligated and used to transform *E. coli* HB 101 or DH-5 to ampicillin resistance. Plasmid pMT2 DNA can be prepared by conventional methods. pMT2 CXM is then constructed using loopout/in mutagenesis [Morinaga, et al., *Biotechnology* 84: 636 (1984). This removes bases 1075 to 1145 relative to the Hind III site near the SV40 origin of replication and enhancer sequences of pMT2. In addition it inserts the following sequence:

5'PO-CATGGGCAGCTCGAG-3' at nucleotide 1145. This sequence contains the recognition site for the restriction endonuclease Xho I. A derivative of pMT2CXM, termed pMT23, contains recognition sites for the restriction endonucleases PstI, Eco RI, SalI and XhoI. Plasmid pMT2 CXM and pMT23 DNA may be prepared by conventional methods.

pEMC2βderived from pMT21 may also be suitable in practice of the invention. pMT21 is derived from pMT2 which is derived from pMT2-VWF. As described above EcoRI digestion excises the cDNA insert present in pMT-VWF, yielding pMT2 in linear form which can be ligated and used to transform *E. Coli* HB 101 or DH-5 to ampicillin resistance. Plasmid pMT2 DNA can be prepared by conventional methods.

pMT21 is derived from pMT2 through the following two modifications. First, 76 bp of the 5' untranslated region of the DHFR cDNA including a stretch of 19 G residues from G/C tailing for cDNA cloning is deleted. In this process, a XhoI site is inserted to obtain the following sequence immediately upstream from DHFR: 5' -CTGCAGGCGAGCCTGAATTCCTCGAGCCATCATG-3'
              PstI              Eco RI XhoI Second, a unique ClaI site is introduced by digestion with EcoRV and XbaI, treatment with Klenow fragment of DNA polymerase I, and ligation to a ClaI linker (CATCGATG). This deletes a 250 bp segment from the adenovirus associated RNA (VAI) region but does not interfere with VAI RNA gene expression or function. pMT21 is digested with EcoRI and XhoI, and used to derive the vector pEMC2B1.

A portion of the EMCV leader is obtained from pMT2-ECAT1 [S. K. Jung, et al, *J. Virol* 63:1651–1660 (1989)] by digestion with Eco RI and PstI, resulting in a 2752 hp fragment. This fragment is digested with TaqI yielding an Eco RI-TaqI fragment of 508 bp which is purified by electrophoresis on low melting agarose gel. A 68 bp adapter and its complementary strand are synthesized with a 5' TaqI protruding end and a 3' XhoI protruding end which has the following sequence:

5'-CGAGGTTAAAAAACGTCTAGGCCCCCCGAACCACGGGGACGTGGTTTTCCTTT
TaqI

GAAAAACACGATTGC-3'
                XhoI

This sequence matches the EMC virus leader sequence from nucleotide 763 to 827. It also changes the ATG at position 10 within the EMC virus leader to an ATT and is followed by a XhoI site. A three way ligation of the pMT21 Eco RI-XhoI fragment, the EMC virus EcoRI-TaqI fragment, and the 68 bp oligonucleotide adapter TaqI-XhoI adapter resulting in the vector pEMC2β1.

This vector contains the SV40 origin of replication and enhancer, the adenovirus major late promoter, a cDNA copy of the majority of the adenovirus tripartite leader sequence, a small hybrid intervening sequence, an SV40 polyadenylation signal and the adenovirus VA I gene, DHFR and β-lactamase markers and an EMC sequence, in appropriate relationships to direct the high level expression of the desired cDNA in mammalian cells.

The construction of vectors may involve modification of the BMP-15-related DNA sequences. For instance, BMP-15 cDNA can be modified by removing the non-coding nucleotides on the 5' and 3' ends of the coding region. The deleted non-coding nucleotides may or may not be replaced by other sequences known to be beneficial for expression. These vectors are transformed into appropriate host cells for expression of BMP-15-related proteins. Additionally, the sequence of SEQ ID NO:1 or SEQ ID NO: 3 or other sequences encoding BMP-15-related proteins can be manipulated to express a mature BMP15-related protein by deleting BMP-15 encoding propeptide sequence and replacing them with sequences encoding the complete propeptides of other BMP proteins.

One skilled in the art can manipulate the sequences of SEQ ID NO: 1 or SEQ ID NO:3 by eliminating or replacing the mammalian regulatory sequences flanking the coding sequence with bacterial sequences to create bacterial vectors for intracellular or extracellular expression by bacterial cells. For example, the coding sequences could be further manipulated (e.g. ligated to other known linkers or modified by deleting non-coding sequences therefrom or altering nucleotides therein by other known techniques). The modified BMP-15-related coding sequence could then be inserted into a known bacterial vector using procedures such as described in T. Taniguchi et al., *Proc. Natl Acad. Sci. USA*, 77:5230–5233 (1980). This exemplary bacterial vector could then be transformed into bacterial host cells and a BMP-15-related protein expressed thereby. For a strategy for producing extracellular expression of BMP-15-related proteins in bacterial cells, see, e.g. European patent application EPA 177,343.

Similar manipulations can be performed for the construction of an insect vector [See, e.g. procedures described in published European patent application 155,476] for expression in insect cells. A yeast vector could also be constructed employing yeast regulatory sequences for intracellular or extracellular expression of the factors of the present invention by yeast cells. [See, e.g., procedures described in published PCT application WO86/00639 and European patent application EPA 123,289].

A method for producing high levels of a BMP-15-related protein of the invention in mammalian cells may involve the construction of cells containing multiple copies of the heterologous BMP-15-related gene. The heterologous gene is linked to an amplifiable marker, e.g. the dihydrofolate reductase (DHFR) gene for which cells containing increased gene copies can be selected for propagation in increasing concentrations of methotrexate (MTX) according to the procedures of Kaufman and Sharp, *J. Mol. Biol.*, 159:601–629 (1982). This approach can be employed with a number of different cell types.

For example, a plasmid containing a DNA sequence for a BMP-15-related protein of the invention in operative association with other plasmid sequences enabling expression thereof and the DHFR expression plasmid pAdA265V(A)3 [Kaufman and Sharp, *Mol. Cell. Biol.*, 2:1304 (1982)] can be co-introduced into DHFR-deficient CHO cells, DUKX-BII, by various methods including calcium phosphate coprecipitation and transfection, electroporation or protoplast fusion. DHFR expressing transformants are selected for growth in alpha media with dialyzed fetal calf serum, and subsequently selected for amplification by growth in increasing concentrations of MTX (e.g. sequential steps in 0.02, 0.2, 1.0 and 5 uM MTX) as described in Kaufman et al., *Mol Cell Biol.*, 5:1750 (1983). Transformants are cloned, and biologically active BMP-15 expression is monitored by the Rosen-modified Sampath-Reddi rat bone formation assay described above in Example 3. BMP-15 protein expression should increase with increasing levels of MTX resistance. BMP-15 polypeptides are characterized using standard techniques known in the art such as pulse labeling with [35S] methionine or cysteine and polyacrylamide gel electrophoresis. Similar procedures can be followed to produce other related BMP-15-related proteins.

Example 5

Biological Activity of Expressed BMP-15

To measure the biological activity of the expressed BMP-15-related proteins obtained in Example 4 above, the proteins are recovered from the cell culture and purified by isolating the BMP-15-related proteins from other proteinaceous materials with which they are co-produced as well as from other contaminants. The purified protein may be assayed in accordance with the rat bone formation assay described in Example 3.

Purification is carried out using standard techniques known to those skilled in the art.

Protein analysis is conducted using standard techniques such as SDS-PAGE acrylamide [Laemmli, *Nature* 227:680 (1970)] stained with silver [Oakley, et al. *Anal. Biochem.* 105:361 (1980)] and by immunoblot [Towbin, et al. *Proc. Natl. Acad. Sci. USA* 76:4350 (1979)]

Example 6

Using Northern analysis, BMP-15 and BMP-15-related proteins can be tested for their effects on various cell lines. Suitable cell lines include cell lines derived from E13 mouse limb buds. After 10 days of treatment with BMP-15 or BMP-15-related protein, the cell phenotype is examined histologically for indications of tissue differentiation. In addition, Northern analysis of mRNA from BMP-15 or BMP-15-related protein treated cells can be performed for various markers including one or more of the following markers for bone, cartilage and/or tendon/ligament, as described in Table IV:

TABLE IV

| Marker | Bone | Cartilage | Tendon/Ligament |
|---|---|---|---|
| Osteocalcin | + | − | − |
| Alkaline Phosphatase | + | − | − |
| Proteoglycan Core Protein | +/−[1] | + | +[2] |
| Collagen Type I | + | + | + |
| Collagen Type II | +/−[2] | + | +[2] |
| Decorin | + | + | + |
| Elastin | +/−[3] | ? | + |

[1] - Marker seen early, marker not seen as mature bone tissue forms
[2] - Marker depends upon site of tendon; strongest at bone interface
[3] - Marker seen at low levels The foregoing descriptions detail presently preferred embodiments of the present invention. Numerous modifications and variations in practice thereof are expected to occur to those skilled in the art upon consideration of these descriptions. Those modifications and variations are believed to be encompassed within the claims appended hereto.

What is claimed is:

1. An isolated DNA sequence encoding a BMP-15-related protein comprising a DNA sequence selected from the group consisting of:
   (a) nucleotides #490 or #634 to #1011 of SEQ ID NO: 1;
   (b) nucleotides #813 or #1002 to #1376 of SEQ ID NO: 3; and
   (c) sequences which hybridize to (a) or (b) under stringent hybridization conditions and encode a protein which exhibits the ability to form cartilage and/or bone and/or other connective tissue.

2. An isolated DNA sequence encoding BMP-15 protein comprising a DNA sequence selected from the group consisting of:
   (a) nucleotides encoding amino acids #-48 or #1 to #125 of SEQ ID NO: 2;
   (b) nucleotides encoding amino acids #-63 or #1 to #125 of SEQ ID NO:4; and
   (c) sequences which hybridize to (a) or (b) under stringent hybridization conditions and encode a protein which exhibits the ability to form cartilage and/or bone and/or other connective tissue.

3. A vector comprising a DNA molecule of claim 1 in operative association with an expression control sequence therefor.

4. A vector comprising a DNA molecule of claim 2 in operative association with an expression control sequence therefor.

5. A host cell transformed with the vector of claim 3.

6. A host cell transformed with the vector of claim 4.

7. An isolated DNA molecule having a sequence encoding a protein which is characterized by the ability to induce the formation of cartilage and/or bone and/or other connective tissue, said DNA molecule comprising a DNA sequence selected from the group consisting of:
   (a) nucleotide #634 to #1008 of SEQ ID NO: 1; and
   (b) nucleotide #1002 to #1376 of SEQ ID NO: 3; and
   (c) naturally occurring allelic sequences and equivalent degenerative codon sequences of (a) or (b).

8. A vector comprising a DNA molecule of claim 7 in operative association with an expression control sequence therefor.

9. A host cell transformed with the vector of claim 8.

10. An isolated DNA molecule encoding BMP-15 protein, said DNA molecule comprising nucleotide #1002 to #1376 of SEQ ID NO: 3.

11. An isolated DNA molecule according to claim 10, further comprising a nucleotide sequence encoding a suitable propeptide 5' to and linked in frame to the DNA coding sequence.

12. A vector comprising a DNA molecule of claim 11 in operative association with an expression control sequence therefor.

13. A host cell transformed with the vector of claim 12.

14. A method for producing purified BMP-15-related protein said method comprising the steps of:
   (a) culturing a host cell transformed with a DNA sequence according to claim 1, comprising a nucleotide sequence encoding BMP-15-related protein; and
   (b) recovering and purifying said BMP-15-related protein from the culture medium.

15. A method for producing purified BMP-15-related protein said method comprising the steps of:
   (a) culturing a host cell transformed with a DNA sequence according to claim 2, comprising a nucleotide sequence encoding BMP-15-related protein; and
   (b) recovering and purifying said BMP-15-related protein from the culture medium.

16. A method for producing purified BMP-15-related protein said method comprising the steps of:
   (a) culturing a host cell transformed with a DNA sequence according to claim 7, comprising a nucleotide sequence encoding BMP-15-related protein; and
   (b) recovering and purifying said BMP-15-related protein from the culture medium.

17. A chimeric DNA molecule comprising a DNA sequence encoding a propeptide from a member of the TGF-β superfamily of proteins linked in correct reading frame to a DNA sequence encoding a BMP-15-related polypeptide.

* * * * *

UNITED STATES PATENT AND TRADEMARK OFFICE
CERTIFICATE OF CORRECTION

PATENT NO. : 5,635,372  Page 1 of 2

DATED : June 3, 1997

INVENTOR(S) : Celeste et al.

It is certified that error appears in the above-identified patent and that said Letters Patent is hereby corrected as shown below:

At column 1, commencing at line 4, please add the sentence --This work was funded in part by grant number CA 48799 from the National Institutes of Health. --

At column 1, lines 35 and 36, please change "protein-s"include" to -- proteins" include --.

At column 2, line 58, please change "WO94/15965 WO94/15949" to -- WO94/15965; WO/15949 --.

At column 4, line 33, please change "BMP/TGF-µ/Vg-1" to -- BMP/TGF-β/Vg-1 --.

At column 4, line 34, please insert a -- . -- after Leu.

At column 8, line 9, please change "TGF-fi" to -- TGF-β --.

At column 8, line 46, please change "to bums" to -- to burns --.

At column 10, line 5, please change "agents ben the" to -- agents beneficial to the treatment of the --.

At column 11, line 22, please delete the word "it".

At column 11, lines 36 and 43, please change "promins" to -- proteins --.

At column 11, line 54, please change "GCGGATCC" to -- GCGGATCC --.

At column 12, line 12, please change "GCTCTAGA" to -- GCTCTAGA --.

At column 12, line 23, please change "BMP/TGF-β/3/Vg-1" to -- "BMP/TGF-β/VG-1--.

At column 13, line 13, please change "#100-#3119" to -- #100-#119 --.

At column 13, line 45, please change "µ/ml" to -- µg/ml --.

At column 13, line 48, please change "an" to -- and --.

At column 14, line 67, please change "inhibin β(B)" to -- inhibin α(B) --.

At column 15, lines 16 and 17, please change "or tem-plates" to -- or genomic DNA templates --.

At column 24, line 49, please change "+/-$^2$" to -- +/-$^1$ --.

UNITED STATES PATENT AND TRADEMARK OFFICE
CERTIFICATE OF CORRECTION

PATENT NO.    :   5,635,372

DATED         :   June 3, 1997

INVENTOR(S)   :   Celeste *et al.*

It is certified that error appears in the above-identified patent and that said Letters Patent is hereby corrected as shown below:

At column 16, line 8, please begin a new paragraph with the sentence commencing "Once a positive . . ."

At column 16, line 44, please change "32p" to -- $^{32}P$ --.

At column 16, line 58, please change "an" to -- and -- .

At column 17, line 26, please change "#489-90 1376" to -- #489-#1376 --.

At column 17, line 33, please change "#498-190 528" to -- #489-#528 --.

At column 17, line 66, please change "sub amino acids" to -- subunit comprising amino acids --.

At column 18, lines 46, 51, and line 62, please change "200/µl" to -- 200 µl --.

At column 18, line 48, please change "100/λg/ml" to -- 100 µg/ml --.

At column 18, line 64, please change "50/µl" to -- 50 µl --.

At column 19, line 10, please change "100/µl" to -- 100 µl --.

At column 20, line 12, please change "mount" to -- amount --.

At column 22, please change "EcoRV" to -- EcoRI --.

At column 23, line 7, please change "sequence" to -- sequences --.

Signed and Sealed this

Seventeenth Day of March, 1998

Attest:

*Attesting Officer*

BRUCE LEHMAN

*Commissioner of Patents and Trademarks*

UNITED STATES PATENT AND TRADEMARK OFFICE
CERTIFICATE OF CORRECTION

PATENT NO. : 5,635,372

DATED : June 3, 1997

INVENTOR(S) : Celeste *et al.*

It is certified that error appears in the above-identified patent and that said Letters Patent is hereby corrected as shown below:

At column 1, line 11 add the following paragraph:

---GOVERNMENT SUPPORT

This invention was made with government support under CA48799 awarded by the National Institutes of Health. The government has certain rights in this invention.--

Signed and Sealed this

Fifteenth Day of May, 2001

Attest:

NICHOLAS P. GODICI

Attesting Officer　　　Acting Director of the United States Patent and Trademark Office

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
        ( A ) LENGTH: 1541 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( B ) STRAIN: PC-3

( i x ) FEATURE:
        ( A ) NAME/KEY: CDS
        ( B ) LOCATION: 157..1008

( i x ) FEATURE:
        ( A ) NAME/KEY: sig_peptide
        ( B ) LOCATION: 157..633

( i x ) FEATURE:
        ( A ) NAME/KEY: mat_peptide
        ( B ) LOCATION: 634..1008

( x i ) SEQUENCE DESCRIPTION: SEQ ID NO:1:

```
ACATTAGTAA AGTGCTCAAT AAAATGATAA AATGCATTAA TATCATGAGC TAATTTTAGG        60

GCTAATTGCA ACTCTCAGTT TACATTCAGA GGTTTTCTAA GGGATGTTCA GTTAAGACAC       120

TAATGGTCTG CCCTGTTCTT TCACATTTGT GCAGGT TCC TGG CAT GTA CAG ACC         174
                                         Ser Trp His Val Gln Thr
                                         -159          -155

CTG GAC TTT CCT CTA GCA TCA AAC CAG GTA GCA TAC GAA CTA ATC AGA         222
Leu Asp Phe Pro Leu Ala Ser Asn Gln Val Ala Tyr Glu Leu Ile Arg
            -150              -145              -140

GCC ACT GTG GTT TAC CGC CAT CAA CTT CAT CTA GTT AAT TAC CAT CTC         270
Ala Thr Val Val Tyr Arg His Gln Leu His Leu Val Asn Tyr His Leu
        -135              -130              -125

TCC TGC CAT GTG GAA ACT TGG GTT CCT AAA TGC CGG ACC AAG CAC TTA         318
Ser Cys His Val Glu Thr Trp Val Pro Lys Cys Arg Thr Lys His Leu
-120              -115              -110

CCT TCT TCT AAA TCG GGT TCC TCA AAG CCT TCT CCC ATG TCT AAA GCC         366
Pro Ser Ser Lys Ser Gly Ser Ser Lys Pro Ser Pro Met Ser Lys Ala
-105              -100              -95               -90

TGG ACA GAG ATA GAT ATT ACA CAT TGT ATT CAG CAG AAG CTC TGG AAT         414
Trp Thr Glu Ile Asp Ile Thr His Cys Ile Gln Gln Lys Leu Trp Asn
                -85              -80               -75

CGC AAG GGA CGG AGT GTT CTT CGC CTC CGC TTC ATG TGT CAG CAG CAA         462
Arg Lys Gly Arg Ser Val Leu Arg Leu Arg Phe Met Cys Gln Gln Gln
            -70              -65               -60

AAA GGC AAT GAG ACT CGT GAG TTC CGG TGG CAT GGC ATG ACA TCC TTG         510
Lys Gly Asn Glu Thr Arg Glu Phe Arg Trp His Gly Met Thr Ser Leu
        -55              -50               -45

GAT GTT GCC TTC TTG CTA CTC TAT TTC AAT GAC ACC GAT GAC AGA GTT         558
Asp Val Ala Phe Leu Leu Leu Tyr Phe Asn Asp Thr Asp Asp Arg Val
    -40              -35               -30

CAG GGT AAA CTT CTT GCA AGA GGC CAA GAG GAG TTA ACT GAT AGG GAA         606
Gln Gly Lys Leu Leu Ala Arg Gly Gln Glu Glu Leu Thr Asp Arg Glu
-25              -20               -15                -10

TCT TCT TTT CTC ATG CGG AGT GTC CGC CAA GCA TGC AGC ATT GAA TCT         654
```

|  |  |  |  |  | Ser | Ser | Phe | Leu | Met<br>-5 | Arg | Ser | Val | Arg | Gln<br>1 | Ala | Cys | Ser | Ile<br>5 | Glu | Ser |  |
|---|---|---|---|---|---|---|---|---|---|---|---|---|---|---|---|---|---|---|---|---|---|

```
GAT GCC TCT TGT CCT TCT CAG GAA CAT GAT GGG TCT GTA AAT AAC CAG          702
Asp Ala Ser Cys Pro Ser Gln Glu His Asp Gly Ser Val Asn Asn Gln
        10              15              20

TGT TCC CTC CAT CCT TAC AAG GTC AGC TTC CAC CAA CTA GGC TGG GAT          750
Cys Ser Leu His Pro Tyr Lys Val Ser Phe His Gln Leu Gly Trp Asp
        25              30              35

CAC TGG ATC ATT GCT CCT CGT CTC TAT ACC CCA AAT TAC TGT AAA GGA          798
His Trp Ile Ile Ala Pro Arg Leu Tyr Thr Pro Asn Tyr Cys Lys Gly
40              45              50                              55

ATC TGT ACT CGG GTA TTA CCC TAT GGT CTC AAT TCA CCC AAC CAT GCC          846
Ile Cys Thr Arg Val Leu Pro Tyr Gly Leu Asn Ser Pro Asn His Ala
                60              65              70

ATC ATT CAG AGC CTT GTC AAT GAA CTA GTG AAT CAC AGT GTA CCT CAG          894
Ile Ile Gln Ser Leu Val Asn Glu Leu Val Asn His Ser Val Pro Gln
            75              80              85

CCT TCC TGT GTC CCT TAT AAT TTT CTT CCT ATG AGC ATC CTC CTG ATT          942
Pro Ser Cys Val Pro Tyr Asn Phe Leu Pro Met Ser Ile Leu Leu Ile
        90              95              100

GAG ACC AAC GGG AGT ATC TTG TAC AAG GAG TAT GAG GGT ATG ATT GCC          990
Glu Thr Asn Gly Ser Ile Leu Tyr Lys Glu Tyr Glu Gly Met Ile Ala
        105             110             115

CAG TCC TGT ACA TGT AGA TAATAGTGAA GTTGTTGCTA TCTCAGGTTT                 1038
Gln Ser Cys Thr Cys Arg
120             125

CCCAAGAAGC TATAGATGTT TAAAGAAAAC TGTGTTAAAG CTGGCAGTGA TCGAGTCGAC        1098

GCCCTATAGT GAGTCGTATT AGAGCTCGCG GCCGCCACCG CGGTGGAGCT CCAATTCGCC        1158

CTATAGTGAG TCGTATTACG CGCGCTCACT GGCCGTCGTT TTACAACGTC GTGACTGGGA        1218

AAACCCTGGC GTTACCCAAC TTAATCGCCT TGCAGCACAT CCCCCTTTCG CCAGCTGGCG        1278

TAATAGCGAA GAGGCCCGCA CCGATCGCCC TTCCCAACAG TTGCGCAGCC TGAATGGCGA        1338

ATGGAAATTG TAAGCGTTAA TATTTTGTTA AAATTCGCGT TAAATTTTTG GTAAATCAGC        1398

TCATTTTTTA ACCAATAGGC CGAAATCGGC AAAATCCCTT ATAAATCAAA AGAATAGACC        1458

AGATAGGGTT GGAGTGTTTG TTCCAGTTTG GGACAAGAG TCCACTATTA AGAACGTGG          1518

GACTCCAACG TCAAAGGGCG AAA                                                1541
```

( 2 ) INFORMATION FOR SEQ ID NO:2:

( i ) SEQUENCE CHARACTERISTICS:
        ( A ) LENGTH: 284 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Ser Trp His Val Gln Thr Leu Asp Phe Pro Leu Ala Ser Asn Gln Val
-159            -155            -150            -145

Ala Tyr Glu Leu Ile Arg Ala Thr Val Val Tyr Arg His Gln Leu His
        -140            -135            -130

Leu Val Asn Tyr His Leu Ser Cys His Val Glu Thr Trp Val Pro Lys
            -125            -120            -115

Cys Arg Thr Lys His Leu Pro Ser Ser Lys Ser Gly Ser Ser Lys Pro
        -110            -105            -100

Ser Pro Met Ser Lys Ala Trp Thr Glu Ile Asp Ile Thr His Cys Ile
-95             -90             -85             -80
```

| Gln | Gln | Lys | Leu | Trp<br>-75 | Asn | Arg | Lys | Gly<br>-70 | Arg | Ser | Val | Leu | Arg | Leu<br>-65 | Arg |

| Phe | Met | Cys | Gln<br>-60 | Gln | Gln | Lys | Gly | Asn<br>-55 | Glu | Thr | Arg | Glu | Phe<br>-50 | Arg | Trp |

| His | Gly | Met<br>-45 | Thr | Ser | Leu | Asp | Val<br>-40 | Ala | Phe | Leu | Leu | Leu<br>-35 | Tyr | Phe | Asn |

| Asp | Thr<br>-30 | Asp | Asp | Arg | Val | Gln<br>-25 | Gly | Lys | Leu | Leu | Ala<br>-20 | Arg | Gly | Gln | Glu |

| Glu<br>-15 | Leu | Thr | Asp | Arg | Glu<br>-10 | Ser | Ser | Phe | Leu | Met<br>-5 | Arg | Ser | Val | Arg | Gln<br>1 |

| Ala | Cys | Ser | Ile<br>5 | Glu | Ser | Asp | Ala | Ser<br>10 | Cys | Pro | Ser | Gln | Glu<br>15 | His | Asp |

| Gly | Ser | Val<br>20 | Asn | Asn | Gln | Cys | Ser<br>25 | Leu | His | Pro | Tyr | Lys<br>30 | Val | Ser | Phe |

| His | Gln<br>35 | Leu | Gly | Trp | Asp | His<br>40 | Trp | Ile | Ile | Ala | Pro<br>45 | Arg | Leu | Tyr | Thr |

| Pro<br>50 | Asn | Tyr | Cys | Lys | Gly<br>55 | Ile | Cys | Thr | Arg | Val<br>60 | Leu | Pro | Tyr | Gly | Leu<br>65 |

| Asn | Ser | Pro | Asn | His<br>70 | Ala | Ile | Ile | Gln | Ser<br>75 | Leu | Val | Asn | Glu | Leu<br>80 | Val |

| Asn | His | Ser | Val<br>85 | Pro | Gln | Pro | Ser | Cys<br>90 | Val | Pro | Tyr | Asn | Phe<br>95 | Leu | Pro |

| Met | Ser | Ile<br>100 | Leu | Leu | Ile | Glu | Thr<br>105 | Asn | Gly | Ser | Ile | Leu<br>110 | Tyr | Lys | Glu |

| Tyr | Glu<br>115 | Gly | Met | Ile | Ala | Gln<br>120 | Ser | Cys | Thr | Cys | Arg<br>125 | | | | |

(2) INFORMATION FOR SEQ ID NO:3:

(i) SEQUENCE CHARACTERISTICS:
        (A) LENGTH: 1609 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (B) STRAIN: hBMP-15

(ix) FEATURE:
        (A) NAME/KEY: CDS
        (B) LOCATION: 531..1376

(ix) FEATURE:
        (A) NAME/KEY: sig_peptide
        (B) LOCATION: 531..1001

(ix) FEATURE:
        (A) NAME/KEY: mat_peptide
        (B) LOCATION: 1002..1376

(xi) SEQUENCE DESCRIPTION: SEQ ID NO:3:

```
AAGCTGCATC TGTATAGTGA TATGACATGA GACTCTTCTT AATCCATGTA TGTTCCAACA    60

ATTCTAAATG GACACATTAA TGGTCAACTA ATAATAATAT TGATCTTCTC CCCTACATAC   120

AGTATGCACA CAAGATAATT CTATATTTGA GTTTTTTCCC CCGAGCCCAG CACTGTAAGT   180

AATCTAACAG TGAGACAGTT TCTCTTAAGA AAACAGACT  TGGGTTCAAA TCTTAACTCT   240

ACCACATACC AGCTGTGTGT CCTTTGTCAT AGCTTCTCTG AGCCTCAATT TCCTTATCTG   300

CAAAATGGGG ATAATAACTA TCTCATAAGA CTATTAAGAA TTAAAGAGCT AATACATGTA   360

AAGCATCTAG TGTATTAGTA AGTGCTCAGT AAATGATAGT ATCATTATCT TGAGTTAATT   420
```

```
TTAGGGCTGA TTATAGCTAT CAGTCTATAT CAAGACAGTT TATGAGGAAT ATTCATGTTA      480

AGAGGTAAGA AGCTAAACCT CTGCTCTTGT TCCCTCTTAC TTCTGCAGGT ACC TGG        536
                                                       Thr Trp
                                                       -157

CAT ATA CAG ATC CTG GGC TTT CCT CTC AGA CCA AAC CGA GGA CTA TAC       584
His Ile Gln Ile Leu Gly Phe Pro Leu Arg Pro Asn Arg Gly Leu Tyr
-155            -150            -145            -140

CAA CTA GTT AGA GCC ACT GTG GTT TAC CGC CAT CAT CTC CAA CTA ACT       632
Gln Leu Val Arg Ala Thr Val Val Tyr Arg His His Leu Gln Leu Thr
                -135            -130            -125

CGC TTC AAT CTC TCC TGC CAT GTG GAG CCC TGG GTG CAG AAA AAC CCA       680
Arg Phe Asn Leu Ser Cys His Val Glu Pro Trp Val Gln Lys Asn Pro
            -120            -115            -110

ACC AAC CAC TTC CCT TCC TCA GAA GGA GAT TCC TCA AAA CCT TCC CTG       728
Thr Asn His Phe Pro Ser Ser Glu Gly Asp Ser Ser Lys Pro Ser Leu
        -105            -100            -95

ATG TCT AAC GCT TGG AAA GAG ATG GAT ATC ACA CAA CTT GTT CAG CAA       776
Met Ser Asn Ala Trp Lys Glu Met Asp Ile Thr Gln Leu Val Gln Gln
    -90            -85            -80

AGG TTC TGG AAT AAC AAG GGA CAC AGG ATC CTA CGA CTC CGT TTT ATG       824
Arg Phe Trp Asn Asn Lys Gly His Arg Ile Leu Arg Leu Arg Phe Met
-75            -70            -65            -60

TGT CAG CAG CAA AAA GAT AGT GGT GGT CTT GAG CTC TGG CAT GGC ACT       872
Cys Gln Gln Gln Lys Asp Ser Gly Gly Leu Glu Leu Trp His Gly Thr
            -55            -50            -45

TCA TCC TTG GAC ATT GCC TTC TTG TTA CTC TAT TTC AAT GAT ACT CAT       920
Ser Ser Leu Asp Ile Ala Phe Leu Leu Leu Tyr Phe Asn Asp Thr His
            -40            -35            -30

AAA AGC ATT CGG AAG GCT AAA TTT CTT CCC AGG GGC ATG GAG GAG TTC       968
Lys Ser Ile Arg Lys Ala Lys Phe Leu Pro Arg Gly Met Glu Glu Phe
        -25            -20            -15

ATG GAA AGG GAA TCT CTT CTC CGG AGA ACC CGA CAA GCA GAT GGT ATC       1016
Met Glu Arg Glu Ser Leu Leu Arg Arg Thr Arg Gln Ala Asp Gly Ile
    -10            -5              1               5

TCA GCT GAG GTT ACT GCC TCT TCC TCA AAA CAT AGC GGG CCT GAA AAT       1064
Ser Ala Glu Val Thr Ala Ser Ser Ser Lys His Ser Gly Pro Glu Asn
            10              15              20

AAC CAG TGT TCC CTC CAC CCT TTC CAA ATC AGC TTC CGC CAG CTG GGT       1112
Asn Gln Cys Ser Leu His Pro Phe Gln Ile Ser Phe Arg Gln Leu Gly
        25              30              35

TGG GAT CAC TGG ATC ATT GCT CCC CCT TTC TAC ACC CCA AAC TAC TGT       1160
Trp Asp His Trp Ile Ile Ala Pro Pro Phe Tyr Thr Pro Asn Tyr Cys
        40              45              50

AAA GGA ACT TGT CTC CGA GTA CTA CGC GAT GGT CTC AAT TCC CCC AAT       1208
Lys Gly Thr Cys Leu Arg Val Leu Arg Asp Gly Leu Asn Ser Pro Asn
    55              60              65

CAC GCC ATT ATT CAG AAC CTT ATC AAT CAG TTG GTG GAC CAG AGT GTC       1256
His Ala Ile Ile Gln Asn Leu Ile Asn Gln Leu Val Asp Gln Ser Val
70              75              80              85

CCC CGG CCC TCC TGT GTC CCG TAT AAG TAT GTT CCA ATT AGT GTC CTT       1304
Pro Arg Pro Ser Cys Val Pro Tyr Lys Tyr Val Pro Ile Ser Val Leu
            90              95              100

ATG ATT GAG GCA AAT GGG AGT ATT TTG TAC AAG GAG TAT GAG GGT ATG       1352
Met Ile Glu Ala Asn Gly Ser Ile Leu Tyr Lys Glu Tyr Glu Gly Met
            105             110             115

ATT GCT GAG TCT TGT ACA TGC AGA TGACAGCAAC AGTACGGCTA GATCAGGTTT      1406
Ile Ala Glu Ser Cys Thr Cys Arg
            120             125

CCCAGGAAAC TGGAGGAGAG TTTAAAATAT CAGTGTTAAA GCTGCAAGTA ATCCTGTACC    1466
```

```
AATCTGTAGG TTATATTTCT TGCCTTAAGT GTTACTTAAG TCTCTTCCCC CACTTGTGAG   1526

CTAGTCAGTT TATAGAAACA GTTCTGATAC CAGTCCCCTA GCATGAATCA GTACAGAGTT   1586

GACACTAATC AGAGCCCTTA ATG                                          1609
```

( 2 ) INFORMATION FOR SEQ ID NO:4:

( i ) SEQUENCE CHARACTERISTICS:
        ( A ) LENGTH: 282 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Thr  Trp  His  Ile  Gln  Ile  Leu  Gly  Phe  Pro  Leu  Arg  Pro  Asn  Arg  Gly
-157       -155                -150                     -145

Leu  Tyr  Gln  Leu  Val  Arg  Ala  Thr  Val  Val  Tyr  Arg  His  His  Leu  Gln
     -140                -135                     -130

Leu  Thr  Arg  Phe  Asn  Leu  Ser  Cys  His  Val  Glu  Pro  Trp  Val  Gln  Lys
-125                -120                     -115                          -110

Asn  Pro  Thr  Asn  His  Phe  Pro  Ser  Ser  Glu  Gly  Asp  Ser  Ser  Lys  Pro
               -105                     -100                          -95

Ser  Leu  Met  Ser  Asn  Ala  Trp  Lys  Glu  Met  Asp  Ile  Thr  Gln  Leu  Val
          -90                     -85                          -80

Gln  Gln  Arg  Phe  Trp  Asn  Asn  Lys  Gly  His  Arg  Ile  Leu  Arg  Leu  Arg
     -75                     -70                          -65

Phe  Met  Cys  Gln  Gln  Gln  Lys  Asp  Ser  Gly  Gly  Leu  Glu  Leu  Trp  His
     -60                     -55                     -50

Gly  Thr  Ser  Ser  Leu  Asp  Ile  Ala  Phe  Leu  Leu  Leu  Tyr  Phe  Asn  Asp
-45                     -40                     -35                          -30

Thr  His  Lys  Ser  Ile  Arg  Lys  Ala  Lys  Phe  Leu  Pro  Arg  Gly  Met  Glu
               -25                     -20                          -15

Glu  Phe  Met  Glu  Arg  Glu  Ser  Leu  Leu  Arg  Arg  Thr  Arg  Gln  Ala  Asp
          -10                      -5                           1

Gly  Ile  Ser  Ala  Glu  Val  Thr  Ala  Ser  Ser  Ser  Lys  His  Ser  Gly  Pro
          5                     10                     15

Glu  Asn  Asn  Gln  Cys  Ser  Leu  His  Pro  Phe  Gln  Ile  Ser  Phe  Arg  Gln
20                      25                     30                          35

Leu  Gly  Trp  Asp  His  Trp  Ile  Ile  Ala  Pro  Pro  Phe  Tyr  Thr  Pro  Asn
               40                      45                          50

Tyr  Cys  Lys  Gly  Thr  Cys  Leu  Arg  Val  Leu  Arg  Asp  Gly  Leu  Asn  Ser
               55                     60                     65

Pro  Asn  His  Ala  Ile  Ile  Gln  Asn  Leu  Ile  Asn  Gln  Leu  Val  Asp  Gln
               70                     75                     80

Ser  Val  Pro  Arg  Pro  Ser  Cys  Val  Pro  Tyr  Lys  Tyr  Val  Pro  Ile  Ser
     85                      90                     95

Val  Leu  Met  Ile  Glu  Ala  Asn  Gly  Ser  Ile  Leu  Tyr  Lys  Glu  Tyr  Glu
100                     105                     110                        115

Gly  Met  Ile  Ala  Glu  Ser  Cys  Thr  Cys  Arg
               120                     125
```

( 2 ) INFORMATION FOR SEQ ID NO:5:

( i ) SEQUENCE CHARACTERISTICS:
        ( A ) LENGTH: 21 amino acids
        ( B ) TYPE: amino acid
        ( C ) STRANDEDNESS: double (D) TOPOLOGY: linear (ii) MOLECULE TYPE: DNA (genomic)

(xi) SEQUENCE DESCRIPTION: SEQ ID NO:5:

```
Thr Arg Pro Xaa Ala Ala Xaa Ala Ala Thr Arg Pro Ile Leu Glu Xaa
 1               5                  10                  15
Ala Ala Ala Leu Ala
            20
```

(2) INFORMATION FOR SEQ ID NO:6:

(i) SEQUENCE CHARACTERISTICS:
        (A) LENGTH: 28 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:6:

GCGGATCCTG GVANGABTGG ATHRTNGC      28

(2) INFORMATION FOR SEQ ID NO:7:

(i) SEQUENCE CHARACTERISTICS:
        (A) LENGTH: 21 amino acids
        (B) TYPE: amino acid
        (C) STRANDEDNESS: double
        (D) TOPOLOGY: linear (ii) MOLECULE TYPE: DNA (genomic)

(xi) SEQUENCE DESCRIPTION: SEQ ID NO:7:

```
Ala Ser Asn His Ile Ser Ala Leu Ala Ile Leu Glu Xaa Ala Ala Gly
 1               5                  10                  15
Leu Asn Thr His Arg
            20
```

(2) INFORMATION FOR SEQ ID NO:8:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

GCTCTAGAGT Y TGNA Y NATN GCRTGRTT      28

(2) INFORMATION FOR SEQ ID NO:9:

(i) SEQUENCE CHARACTERISTICS:
        (A) LENGTH: 119 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 28..99

(xi) SEQUENCE DESCRIPTION: SEQ ID NO:9:

```
GGATCCTGGG AGGATTGGAT TGTGGCT CCT CGT CTC TAT ACC CCA AAT TAC      51
                              Pro Arg Leu Tyr Thr Pro Asn Tyr
```

```
            1                    5
TGT AAA GGA ATC TGT ACT CGG GTA TTA CCC TAT GGT CTC AAT TCA CCC      99
Cys Lys Gly Ile Cys Thr Arg Val Leu Pro Tyr Gly Leu Asn Ser Pro
     10                  15                  20

AACCACGCTA TAGTCCAAAC                                                119
```

( 2 ) INFORMATION FOR SEQ ID NO:10:

( i ) SEQUENCE CHARACTERISTICS:
        ( A ) LENGTH: 24 amino acids
        ( B ) TYPE: amino acid
        ( D ) TOPOLOGY: linear ( i i ) MOLECULE TYPE: protein ( x i ) SEQUENCE DESCRIPTION: SEQ ID NO:10:

```
Pro Arg Leu Tyr Thr Pro Asn Tyr Cys Lys Gly Ile Cys Thr Arg Val
 1               5                  10                  15
Leu Pro Tyr Gly Leu Asn Ser Pro
             20
```

( 2 ) INFORMATION FOR SEQ ID NO:11:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

```
TCCTCGTCTC TATACCCCAA ATTACTGTAA AGGAATCTGT                          40
```

( 2 ) INFORMATION FOR SEQ ID NO:12:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:12:

```
ATCTGTACTC GGGTATTACC CTATGGTCTC AATTCACCC                           39
```

( 2 ) INFORMATION FOR SEQ ID NO:13:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:13:

```
GCTTCCACCA ACTAGGCTGG                                                20
```

( 2 ) INFORMATION FOR SEQ ID NO:14:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear (  i  i  ) MOLECULE TYPE: DNA (  x  i  ) SEQUENCE DESCRIPTION: SEQ ID NO:14:

CTACATGTAC AGGACTGGGC　　　　　　　　　　　　　　　　　　　　　　　　　　　　　　2 0